US012575545B2

(12) United States Patent
Komatsubara et al.

(10) Patent No.: US 12,575,545 B2
(45) Date of Patent: Mar. 17, 2026

(54) PET DIAPER AND METHOD FOR MANUFACTURING SAME

(71) Applicant: Unicharm Corporation, Ehime (JP)

(72) Inventors: Daisuke Komatsubara, Kanonji (JP);
Daichi Fukumoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 4 days.

(21) Appl. No.: 18/465,723

(22) Filed: Sep. 12, 2023

(65) Prior Publication Data

US 2023/0413784 A1 Dec. 28, 2023

Related U.S. Application Data

(63) Continuation of application No. PCT/JP2021/046579, filed on Dec. 16, 2021.

(30) Foreign Application Priority Data

Mar. 19, 2021 (JP) ................................. 2021-046104

(51) Int. Cl.
*A61F 13/15* (2006.01)
*A01K 23/00* (2006.01)

(52) U.S. Cl.
CPC ........ *A01K 23/00* (2013.01); *A61F 13/15723* (2013.01); *A61F 13/15756* (2013.01); *A61F 13/15764* (2013.01); *A61F 13/15804* (2013.01); *A61F 2013/15715* (2013.01); *A61F 2013/15991* (2013.01)

(58) Field of Classification Search
CPC ...................... A61K 23/00; A61F 2013/15186
USPC ................................................... 604/385.09
See application file for complete search history.

(56) References Cited

U.S. PATENT DOCUMENTS

| | | | | | |
|---|---|---|---|---|---|
| 5,954,015 | A | * | 9/1999 | Ohta | ...................... A01K 23/00 |
| | | | | | 119/850 |
| 9,023,006 | B2 | * | 5/2015 | Takino | .............. A61F 13/49011 |
| | | | | | 604/385.24 |
| 9,439,812 | B2 | * | 9/2016 | Komatsubara | .... A61F 13/49014 |

(Continued)

FOREIGN PATENT DOCUMENTS

| | | |
|---|---|---|
| JP | 2003-210062 A | 7/2003 |
| JP | 5785032 B2 | 9/2015 |

(Continued)

OTHER PUBLICATIONS

International Preliminary Report on Patentability issued in corresponding International Application No. PCT/JP2021/046579, dated Sep. 28, 2023, 6 pages.

(Continued)

*Primary Examiner* — Catharine L Anderson
(74) *Attorney, Agent, or Firm* — Osha Bergman Watanabe & Burton LLP

(57) ABSTRACT

A pet diaper extending in a lateral direction along a waist of a pet and in a longitudinal direction from a ventral side to a dorsal side of the pet, the lateral direction being orthogonal to the longitudinal direction, and the pet diaper including: a main body including an absorbent core and a tail hole configured to pass feces of the pet; and a first elastic string attached to the main body in a stretched state and extending at least from a ventral-side edge of the tail hole and a dorsal-side edge of the absorbent core in the longitudinal direction.

12 Claims, 16 Drawing Sheets

(56)                    References Cited

U.S. PATENT DOCUMENTS

| | | | |
|---|---|---|---|
| 9,894,881 B2 * | 2/2018 | Komatsubara .... | A61F 13/49017 |
| 11,229,189 B2 * | 1/2022 | Komatsubara ............ | B32B 5/18 |
| 2018/0014508 A1 * | 1/2018 | Fang ................... | A01K 13/006 |
| 2018/0271064 A1 * | 9/2018 | Komatsubara .... | A61F 13/49058 |
| 2020/0368080 A1 | 11/2020 | Komatsubara | |

FOREIGN PATENT DOCUMENTS

| | | | |
|---|---|---|---|
| JP | 3203207 | U | 3/2016 |
| JP | 6232688 | B1 | 11/2017 |
| JP | 2020-080833 | A | 6/2020 |
| JP | 2020-188749 | A | 11/2020 |

OTHER PUBLICATIONS

Extended European Search Report issued in corresponding European Patent Application No. 21931734.4, dated Jan. 24, 2025 (15 pages).

* cited by examiner

PET DIAPER AND METHOD FOR MANUFACTURING SAME

BACKGROUND

Technical Field

The present disclosure relates to a pet diaper and a method for manufacturing the same.

Description of Related Art

Patent Literature 1 discloses a pet diaper to be worn by a pet such as a dog or a cat. The pet diaper disclosed in Patent Literature 1 includes a diaper main body in which a tail hole allowing feces excreted by a pet to pass therethrough is formed in a rump contact portion covering the rump of the pet, and a feces bag which collects feces passing through the tail hole. This pet diaper prevents feces from adhering to fur or the like of a pet by absorbing urine with a water absorbent of the diaper main body and collecting feces in the feces bag.

[Patent Literature 1] Japanese Patent No. 6232688

The tail hole formed in the pet diaper of Patent Literature 1 needs to be maintained at a position facing the anus of a pet in order for feces to pass therethrough. However, for example, when a pet actively moves, such as during a walk, the position of the tail hole may be displaced due to occurrence of displacement of the pet diaper. Particularly, when a gap is generated between an edge of the tail hole and the rump of a pet due to displacement of the pet diaper, there is concern that feces may enter the inside of the pet diaper through the gap and adhere to the pet.

SUMMARY

Hence, one or more embodiments of the present invention provide a pet diaper with which feces are unlikely to adhere to a pet.

A pet diaper according to an aspect extends in a lateral direction along a waist of a pet and in a longitudinal direction from a ventral side to a dorsal side of the pet, the lateral direction being orthogonal to the longitudinal direction. The pet diaper has a main body including an absorbent core and a tail hole configured to pass feces of the pet. The pet diaper further comprises an elastic member (i.e., an elastic string or a first elastic string) attached to the main body in a stretched state and extending at least from a ventral-side edge of the tail hole to a dorsal-side edge of the absorbent core in the longitudinal direction.

In the pet diaper according to the foregoing aspect, since the elastic member extends between at least the edge of the tail hole on the ventral side and the edge of the absorbent core on the dorsal side, a region between the tail hole and the absorbent core in the main body is pulled to the absorbent core side due to elasticity of the elastic member and is pressed against the rump of the pet. Accordingly, fitting properties of the pet diaper are improved, and a gap is unlikely to be generated between the edge of the tail hole and the rump of the pet. Therefore, feces are unlikely to enter the inside of the pet diaper, and thus feces are unlikely to adhere to the pet.

In one aspect, the main body may further include a tongue piece configured to cover or uncover the tail hole. The tongue piece may include a base end portion coupled to a dorsal-side edge of the tail hole, and a distal end portion opposite to the base end portion, wherein the tongue piece uncovers the tail hole when folded back with the base end portion as a starting point (or a fold line). The distal end portion of the tongue piece may be directed to the ventral side or in the lateral direction when the tongue piece is not folded back. In this aspect, since the distal end portion of the tongue piece is directed to the ventral side or in the lateral direction, the tongue piece is prevented from being disposed below the anus of the pet when being folded back with the base end portion as a fold line. Therefore, adhesion of feces to the pet diaper at the time of excretion is suppressed.

In one aspect, the tail hole may be formed by cutting out a part of the main body. In this aspect, since the tongue piece described above is prevented from being disposed below the anus of the pet, adhesion of feces to the pet diaper at the time of excretion is suppressed.

In one aspect, the dorsal-side edge of the absorbent core may be disposed closer to the ventral side than is the ventral-side edge of the tail hole. In this aspect, regions in which the absorbent core is not disposed are formed on both sides of the tail hole in the lateral direction and the dorsal side. These regions are flexibly deformed along the rump of the pet due to a reduced rigidity corresponding to that of the absorbent core. Therefore, fitting properties of the pet diaper are further improved, and thus a gap is unlikely to be generated between the edge of the tail hole and the rump of the pet.

In one aspect, an opening width of the tail hole in the lateral direction may continuously narrow toward the ventral side. Since a width of the anus at the time of defecation is larger than a width of feces, feces can pass therethrough while having a small opening area of the tail hole by causing the opening width of the tail hole in the lateral direction to narrow toward the ventral side. In addition, leakage of urine through the tail hole can be suppressed by having a small opening area of the tail hole.

In one aspect, the elastic member may extend beyond a central position of the tail hole in the longitudinal direction. In this aspect, since a region on the outer side of the tail hole of the main body in the lateral direction is pressed against the rump of the pet due to contraction of the elastic member, fitting properties of the pet diaper can be further improved.

In one aspect, the elastic member may extend beyond the dorsal-side of the tail hole in the longitudinal direction. In this aspect, since a region on the dorsal side of the tail hole of the main body is pressed against the rump of the pet due to contraction of the elastic member, fitting properties of the pet diaper can be further improved.

In one aspect, the elastic member may extend beyond a ventral-side edge of a virtual tail hole, wherein the virtual tail hole is set at a position line-symmetrical to the tail hole with respect to a center line of the main body in the longitudinal direction. In this aspect, since the elastic member extends to the ventral side over the center line, a region on the ventral side of the main body is pressed against the ventral portion of the pet due to contraction of the elastic member. Therefore, fitting properties of the pet diaper can be further improved.

The pet diaper according to the aspect may further include a pair of fastening tabs that are disposed closer to the ventral side than is the tail hole, and that extend outside lateral-side edges of the main body; and a target portion that is disposed closer to the dorsal side than is the tail hole to be engaged with the pair of fastening tabs. The elastic member may extend beyond dorsal-side edges of the pair of fastening tabs in the longitudinal direction. In this aspect, since the elastic member extends beyond the edges of the pair of fastening tabs on the dorsal side, the elastic member is stretched to the ventral side when the pair of fastening tabs are pulled up to be engaged with the target portion, and thus the main body is pressed against the pet due to a contractile force of the elastic member. Therefore, fitting properties of the pet diaper can be further improved.

According to the aspect, the elastic member may extend beyond a ventral-side edge of the target portion in the longitudinal direction. Generally, a pet such as a dog or a cat adopts a posture with a protruding rump and a rounded dorsal portion at the time of defecation. In this aspect, since the elastic member extends beyond the edge of the target portion on the ventral side, a tensile force acts on a region on the dorsal side of the main body and the elastic member is stretched when the pet has the rounded dorsal portion at the time of defecation, and thus the main body is pressed against the pet due to a contractile force of the elastic member. Therefore, fitting properties of the pet diaper can be further improved.

The pet diaper according to the aspect may further include a waist gather that is disposed closer to the ventral side than are the dorsal-side edges of the pair of fastening tabs, and that is stretchable in the lateral direction. The elastic member may extend beyond a dorsal-side edge of the waist gather. In this aspect, since the elastic member extends beyond the edge of the waist gather on the dorsal side, the elastic member is stretched to the ventral side due to contraction of the waist gather. As a result, since a contractile force of the elastic member is enhanced and the pet diaper is pressed against the pet, fitting properties of the pet diaper are improved.

In one aspect, the pet diaper may further include a leakproof gather disposed at a position outside the absorbent core in the lateral direction. The elastic member may be disposed at a position outside the leakproof gather in the lateral direction. In this aspect, since the elastic member is disposed at a position outside the leakproof gather in the lateral direction, the side edge of the main body in the lateral direction can be arranged around the legs of the pet in a tight contact manner. Therefore, fitting properties of the pet diaper can be further improved.

In one aspect, the leakproof gather may include a second elastic member (i.e., a second elastic string) that extends in the longitudinal direction, a standing portion that stands upright by contraction of the second elastic member, and a vertical fixed portion that serves as a standing fulcrum of the standing portion in the longitudinal direction. The vertical fixed portion may be fixed to the main body at a position outside the absorbent core in the longitudinal direction. In this aspect, since the standing portion of the leakproof gather is disposed in a state of standing upright at a position outside the absorbent core in the lateral direction, leakage of urine can be suppressed.

In one aspect, a stretch ratio of the elastic member may be higher than a stretch ratio of the second elastic member. In this aspect, since the elastic member having a relatively strong contractile force is disposed at a position outside the leakproof gather in the lateral direction, the side edge of the main body can be brought into tighter contact around the legs of the pet. Therefore, fitting properties of the pet diaper can be improved.

In one aspect, an effective length of the elastic member may be longer than an effective length of the second elastic member, and a largest opening width of the tail hole in the lateral direction may be smaller than a distance between a center line of the main body in the lateral direction and an inner edge of the leakproof gather in the lateral direction. In this aspect, since the effective length of the elastic member is longer than the effective length of the second elastic member, even when the second elastic member is cut due to strenuous movement or the like of the pet, the pet diaper can be fitted to the pet due to a contractile force of the elastic member.

In one aspect, a distance between the dorsal-side edge of the tail hole and the dorsal-side edge of the absorbent core in the longitudinal direction may be longer than a distance between a lateral-side edge of the tail hole and the elastic member in the lateral direction. In this aspect, the distance between the edge of the tail hole on the dorsal side and the edge of the absorbent core on the dorsal side is set to be relatively long. Since the absorbent core is not disposed and the rigidity is low in a region between the edge of the tail hole on the dorsal side and the edge of the absorbent core on the dorsal side in the main body, the pet diaper can be fitted to the pet by setting the length of this region to be comparatively long.

In one aspect, there is provided a method for continuously manufacturing a pet diaper extending in a lateral direction along a waist of a pet and in a longitudinal direction from a ventral side to a dorsal side of the pet, the lateral direction being orthogonal to the longitudinal direction. This method for manufacturing the pet diaper including conveying, in a conveyance direction along the longitudinal direction, a strip-shaped top sheet (or a belt-shaped top sheet) composed of top sheets continuous with each other in the longitudinal direction, and a strip-shaped back sheet (or a belt-shaped back sheet) composed of back sheets continuous with each other in the longitudinal direction; attaching a pair of elastic members (i.e., a pair of elastic strings) to the strip-shaped back sheet in a stretched state in the longitudinal direction; forming a main body complex including: the strip-shaped top sheet; the strip-shaped back sheet to which the pair of elastic members are attached; and a plurality of the absorbent cores arranged at a predetermined interval in the longitudinal direction between the strip-shaped top sheet and the strip-shaped back sheet; forming a tail hole by cutting the main body complex along a cutting line at a position between the pair of elastic members; and after forming the tail hole, cutting the main body complex including the pair of elastic members along the lateral direction to form the pet diaper including each of the top sheets, each of the back sheets, and each of the absorbent cores. The cutting line has substantially a U-shape opening in a direction opposite to the conveyance direction, substantially a U-shape opening in the lateral direction, or a ring shape.

In the method for manufacturing a pet diaper according to the foregoing aspect, since the pair of elastic members are fixed to the strip-shaped back sheet in a state of being stretched in the longitudinal direction, when a pet diaper is formed by cutting the main body complex, the pet diaper contracts in the longitudinal direction due to contractile forces of the pair of elastic members. It is not easy to form a neat continuous tail hole having no distortion in a contracted pet diaper. In contrast, in the method for manufacturing a pet diaper described above, since the main body complex is cut together with the pair of elastic members after the tail hole is formed, a neat tail hole can be formed.

In one aspect, the method for manufacturing a pet diaper according to the aspect may further include, when forming the tail hole, or after forming the tail hole, forming a pair of leg opening portions in the main body complex, wherein the pair of leg opening portions are configured to pass hind legs of the pet. In this aspect, a neat tail hole can be formed.

In one aspect, the tail hole may be formed at a position not overlapping the absorbent core. A neat tail hole can be formed by forming a tail hole at a position not overlapping the absorbent core having a high rigidity.

In one aspect, the strip-shaped back sheet may include strip-shaped back non-woven fabric (or belt-shaped back non-woven fabric) and a liquid-impermeable strip-shaped back film (or a liquid-impermeable belt-shaped back film) disposed between the strip-shaped back non-woven fabric and the strip-shaped top sheet. The main body complex may include a bonded region where the strip-shaped top sheet and the strip-shaped back film are directly bonded to each other, and a non-bonded region where the strip-shaped top sheet and the strip-shaped back film are not directly bonded to each other. The tail hole may be formed in the bonded region. In this aspect, a neat tail hole can be formed by forming a tail hole in the bonded region where creases are unlikely to be formed.

In one aspect, the main body complex may further include: a pair of fastening tabs, and a target portion engaged with the pair of fastening tabs. The tail hole may be formed between the absorbent core and the target portion in the longitudinal direction. In a region between the absorbent core and the target portion, since creases are unlikely to be formed in the main body complex due to the rigidity of the absorbent core, a neat tail hole can be formed by forming a tail hole between the absorbent core and the target portion.

According to various aspects of the present invention, adhesion of feces to a pet can be suppressed.

DETAILED DESCRIPTION OF EMBODIMENTS

Hereinafter, with reference to the drawings, embodiments of the present disclosure will be described. In the following description, the same reference signs are applied to elements which are the same or corresponding, and duplicate description thereof will not be repeated. Dimensional ratios of the drawings do not necessarily coincide with those in the description.

Figure 1:
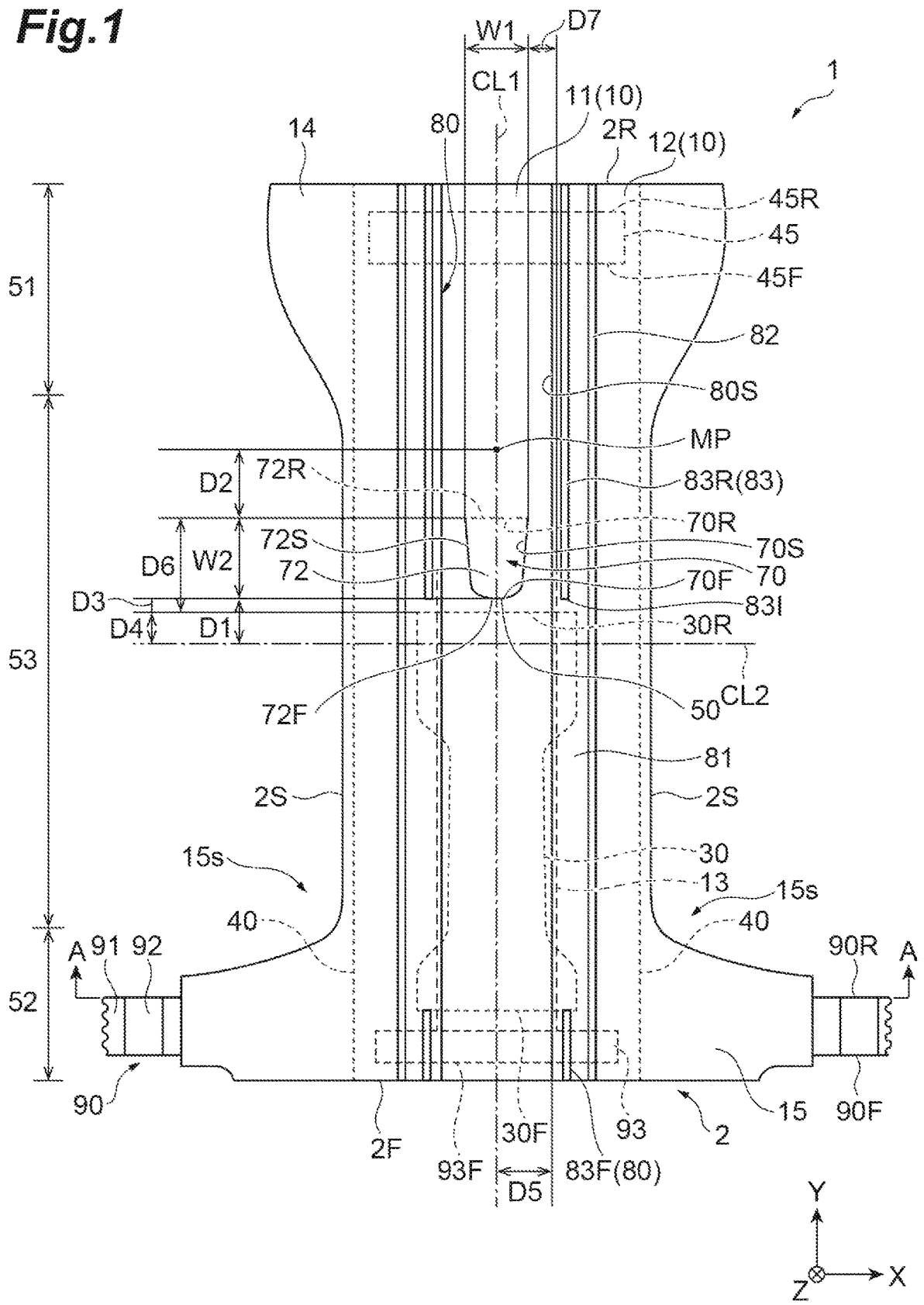
FIG. 1 is a plan view illustrating a pet diaper according to one or more embodiments.
Figure 2:
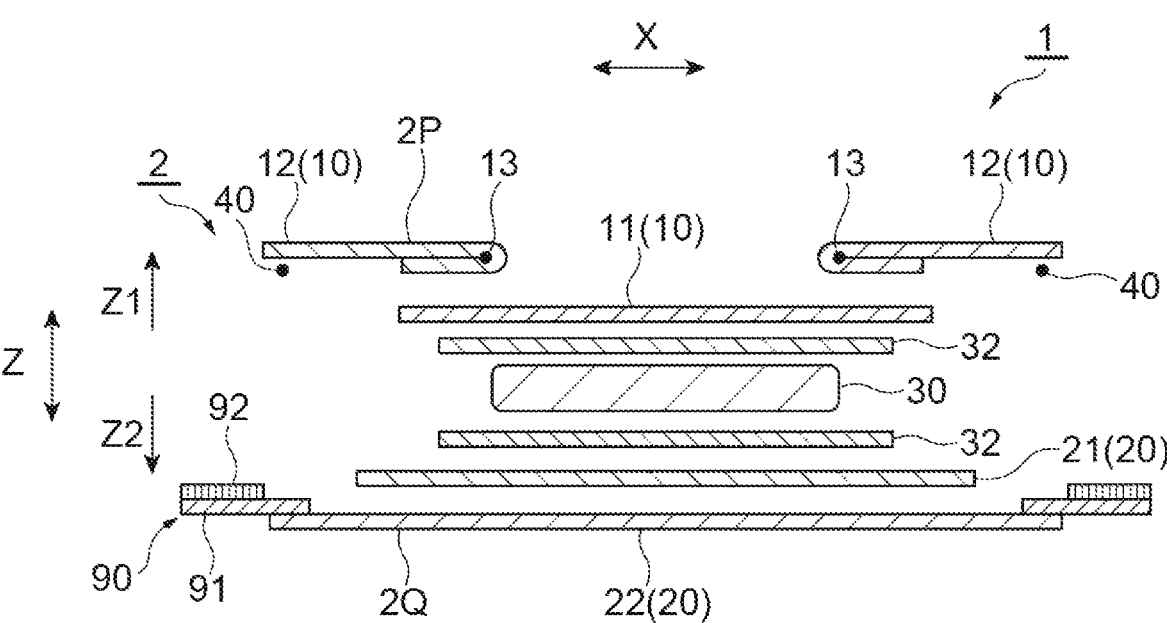
FIG. 2 is a cross-sectional view schematically illustrating the pet diaper along line A-A in FIG. 1.

FIG. 1 is a plan view of a pet diaper according to one or more embodiments viewed from a front surface side Z1. FIG. 2 is a cross-sectional view schematically illustrating the pet diaper along line A-A indicated in FIG. 1. FIGS. 1 and 2 illustrate a pet diaper 1 in a stretched state where the pet diaper 1 is stretched to a state where no creases are formed. In the following description, a positional relationship in a stretched state will be described unless otherwise specified. In addition, in the cross-sectional view illustrated in FIG. 2, for the sake of convenience of description, the members are illustrated with a space therebetween in a thickness direction Z, but they are in contact with each other in the thickness direction Z in an actual product.

Figure 3:
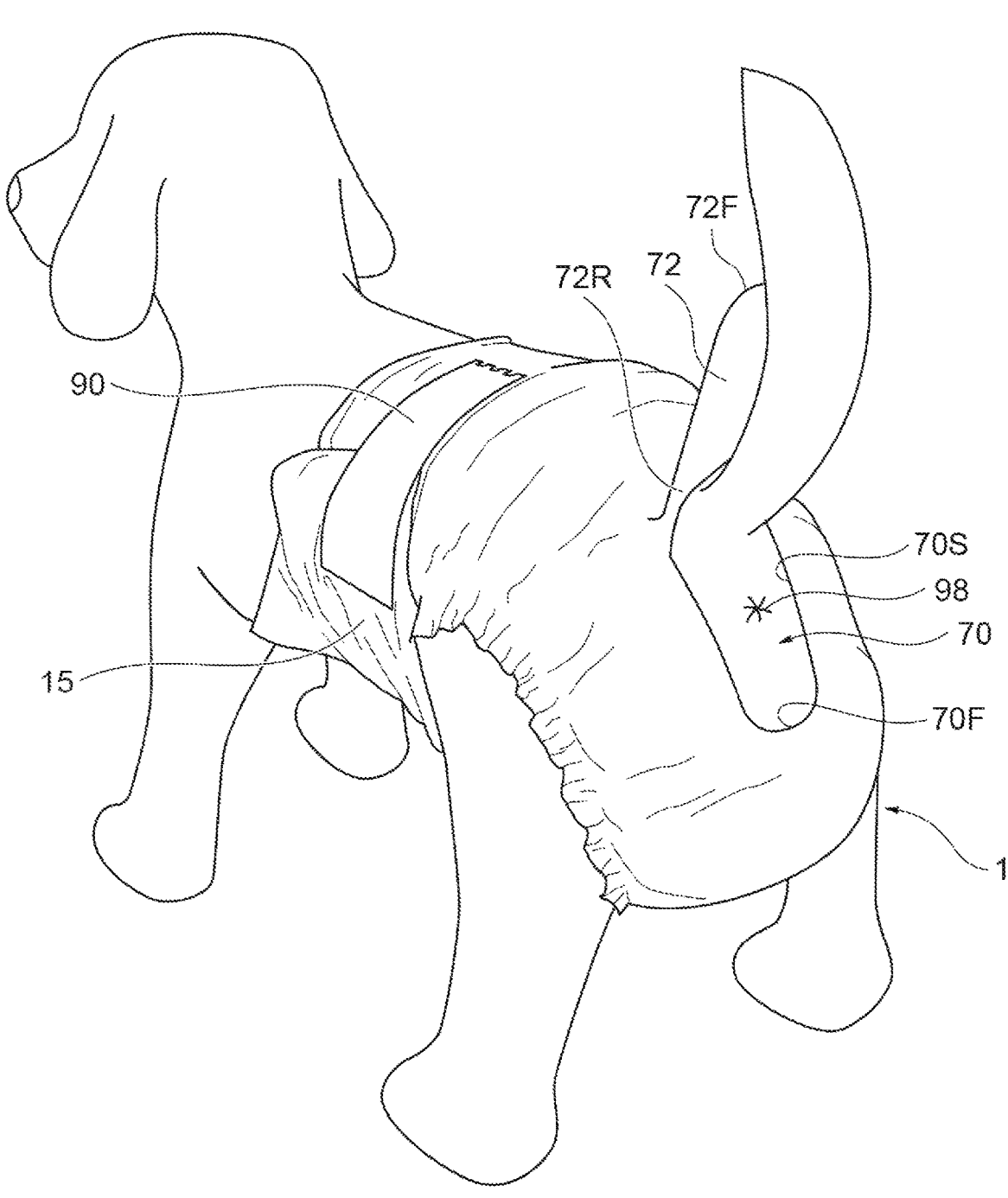
FIG. 3 is a view illustrating a state where the pet diaper is worn.

The pet diaper 1 is a diaper used for a pet. In this specification, "a pet" extensively includes vertebrates and invertebrates and typically includes pet animals such as a dog, a cat, a rabbit, and a hamster. The pet diaper 1 of one or more embodiments is a diaper for a dog or a cat. This pet diaper 1 is favorably utilized at the time of a walk of a pet. As illustrated in FIG. 1, the pet diaper 1 extends in a lateral direction X disposed in a girth direction of a pet and in a longitudinal direction Y orthogonal to the lateral direction X. The longitudinal direction Y is a direction in which a ventral side of a pet is connected to a dorsal side thereof. The thickness direction Z is a direction orthogonal to the lateral direction X and the longitudinal direction Y and includes the front surface side Z1 brought into contact with a pet in a worn state and a rear surface side Z2 directed to an outward side in a worn state. As illustrated in FIG. 3, the pet diaper according to one or more embodiments is worn such that a pet is covered from the ventral side to the dorsal side through the crotch.

The pet diaper 1 has a main body 2. The main body 2 includes at least a top sheet 10, a back sheet 20, and an absorbent core 30. The top sheet 10 constitutes a surface brought into contact with a pet in the main body 2 and is disposed on the front surface side Z1. The top sheet 10 has liquid permeability allowing a body fluid to permeate it to the absorbent core 30 side. The top sheet 10 includes a center sheet 11 positioned at the center in the longitudinal direction Y and covering the absorbent core 30, and side sheets 12 covering both side portions of the center sheet 11 in the lateral direction X. As illustrated in FIG. 2, inward parts of the side sheets 12 in the lateral direction X are folded back to the rear surface side Z2. Elastic members or elastic strings (second elastic strings) 13 in a state of being stretched in the longitudinal direction Y are disposed between the folded-back side sheets 12. The side sheets 12 and the elastic members 13 constitute leakproof gathers 80. The leakproof gathers 80 are orthostatic leakproof gathers and are disposed on the front surface side Z1 from the absorbent core 30. Details of the leakproof gathers 80 will be described below.

The back sheet 20 constitutes a surface positioned on the outward side in the main body 2 when worn and is disposed on the rear surface side Z2. The back sheet 20 includes a liquid-impermeable back film 21 and a back non-woven fabric 22 positioned on the rear surface side Z2 from the back film 21. In one or more embodiments, the back non-woven fabric 22 may be disposed on the front surface side Z1 from the back film 21. A length of the back film 21 in the lateral direction X may be formed to be shorter than a length of the back non-woven fabric 22 in the lateral direction X, and the back non-woven fabric 22 may extend to both sides in the lateral direction X from the back film 21.

The absorbent core 30 is disposed between the top sheet 10 and the back sheet 20. For example, the absorbent core 30 includes plant-derived pulp and a super absorbent polymer (SAP) and absorbs urine of a pet, for example. As illustrated in FIG. 2, an upper surface and a lower surface of the absorbent core 30 may be covered by a core wrap 32. The absorbent core 30 is disposed substantially at the center of the main body 2 in the lateral direction X. A width of the absorbent core 30 in the lateral direction X is shorter than a width of the main body 2 in the lateral direction X. In addition, the width of the absorbent core 30 in the lateral direction X may partially narrow at a position between an edge 30R of the absorbent core 30 on the dorsal side and an edge 30F of the absorbent core 30 on the ventral side.

The edge 30R of the absorbent core 30 on the dorsal side is disposed on the dorsal side from a center line CL2 of the main body 2 in the longitudinal direction Y. The edge 30F of the absorbent core 30 on the ventral side is disposed on the dorsal side from a ventral side edge 2F, which will be described below. That is, a length of the absorbent core 30 in the longitudinal direction Y is shorter than a length of the main body 2 in the longitudinal direction Y. In addition, the edge 30R of the absorbent core 30 on the dorsal side is disposed on the ventral side from an edge 70F of a tail hole 70 on the ventral side, which will be described below.

The main body 2 has a dorsal side edge 2R positioned on the dorsal side in the longitudinal direction Y, and the ventral side edge 2F positioned on the ventral side in the longitudinal direction Y. The dorsal side edge 2R is disposed on the dorsal side in the girth direction of a pet when worn, and the ventral side edge 2F is disposed on the ventral side in the girth direction of a pet when worn. In addition, the main body 2 has a dorsal side area 51 positioned on the dorsal side edge 2R side, a ventral side area 52 positioned on the ventral side edge 2F side, and an intermediate area 53 positioned between the dorsal side area 51 and the ventral side area 52 in the longitudinal direction Y. A pair of extending portions 14 protruding to the outward side in the lateral direction X from the main body 2 are formed in the dorsal side area 51 of the main body 2. A pair of extending portions 15 protruding to the outward side in the lateral direction X from the main body 2 are formed in the ventral side area 52 of the main body 2. The pair of extending portions 15 define a pair of leg opening portions 15s for allowing the hind legs of a pet to pass therethrough.

A pair of fastening tabs 90 are respectively provided in the pair of extending portions 15. The pair of fastening tabs 90 extend to the outward side in the lateral direction X from the main body 2 in the vicinity of the ventral side edge 2F of the main body 2 in the longitudinal direction Y. The pair of fastening tabs 90 may respectively have base material sheets 91 joined to the extending portions 15, and joint portions 92 provided on the base material sheets 91. The joint portions 92 are disposed on surfaces of the fastening tabs 90 on the front surface side Z1. For example, the joint portions 92 are mechanical fasteners, which are constituted to be able to be joined to a target portion 45 formed on the rear surface side Z2 of the main body 2. The pair of fastening tabs 90 are provided on the ventral side from the tail hole 70 (which will be described below), and the target portion 45 is provided on the dorsal side from the tail hole 70. In one or more embodiments, the main body 2 may not include the target portion 45, and the joint portions 92 of the pair of fastening tabs 90 may be constituted to be directly joined to the rear surface side Z2 of the back sheet 20.

In addition, a waist gather 93 stretchable in the lateral direction X may be provided in the vicinity of the ventral side edge 2F of the main body 2. For example, the waist gather 93 is disposed on the ventral side from edges 90R of the pair of fastening tabs 90 on the dorsal side and brings the ventral side area 52 into tight contact with the ventral portion of a pet by being stretched in the lateral direction.

The tail hole 70 is formed in the main body 2. For example, the tail hole 70 is an opening portion having substantially a tongue shape formed in the main body 2 by making a cut 50 having substantially a U-shape opening on the dorsal side of the main body 2. The tail hole 70 is utilized as an excretion hole through which the tail of a pet can be inserted and feces of a pet can pass. The tail hole 70 has a vertically elongated shape in which a largest opening width W2 in the longitudinal direction Y is larger than a largest opening width W1 in the lateral direction X. The largest opening width W1 of the tail hole 70 in the lateral direction X is designed to be larger than a width of an anus 98 of a pet (refer to FIG. 3). In one or more embodiments, an opening width of the tail hole 70 in the lateral direction X may continuously narrow toward the ventral side.

In the embodiments illustrated in FIG. 1, an edge 70R of the tail hole 70 on the dorsal side and the edge 70F of the tail hole 70 on the ventral side are disposed on the dorsal side from the center line CL2 of the main body 2 in the longitudinal direction Y. The center line CL2 is a virtual line positioned at an equal distance from the dorsal side edge 2R and the ventral side edge 2F and extending in the lateral direction X. That is, the center line CL2 is a part in which a folded line is formed when the pet diaper 1 is folded in half in the longitudinal direction Y, and a region on the ventral side from the center line CL2 of the main body 2 is brought into contact with an urination opening of a pet when the pet wears the pet diaper 1.

As illustrated in FIG. 1, the edge 70R of the tail hole 70 on the dorsal side is disposed on the ventral side from a middle point MP between the center line CL2 of the main body 2 and an edge 45F of the target portion 45 on the ventral side in the longitudinal direction Y. In one or more embodiments, the largest opening width W2 of the tail hole 70 in the longitudinal direction Y may be larger than a distance D1 between the edge 70F of the tail hole 70 on the ventral side and the center line CL2 of the main body 2 in the longitudinal direction Y. In addition, the largest opening width W2 of the tail hole 70 in the longitudinal direction Y may be larger than a distance D2 between the edge 70R of the tail hole 70 on the dorsal side and the middle point MP. Specifically, the largest opening width W2 of the tail hole 70 in the longitudinal direction Y may be 35 mm to 80 mm and may be more preferably 40 mm to 80 mm. Moreover, the distance D1 between the edge 70F of the tail hole 70 on the ventral side and the center line CL2 of the main body 2 in the longitudinal direction Y may be shorter than the distance D2 between the edge 70R of the tail hole 70 on the dorsal side and the middle point MP.

In addition, the edge 70F of the tail hole 70 on the ventral side is formed on the dorsal side from the edge 70R of the absorbent core 30 on the dorsal side. Therefore, regions in which the absorbent core 30 is not disposed are formed on the outward side of the tail hole 70 of the main body 2 in the lateral direction X and the dorsal side of the tail hole 70 of the main body 2. In one or more embodiments, a distance D3 between the edge 70F of the tail hole 70 on the ventral side and the edge 70R of the absorbent core 30 on the dorsal side may be shorter than a distance D4 between the edge 30R of the absorbent core 30 on the dorsal side and the center line CL2 of the main body 2 in the longitudinal direction Y. That is, the edge 30R of the absorbent core 30 on the dorsal side is disposed at a position close to the edge 70F of the tail hole 70 on the ventral side.

The tail hole 70 is formed on a center line CL1 of the main body 2 in the lateral direction X. The center line CL1 is a virtual line positioned at an equal distance from a pair of side edges 2S of the main body 2 in the lateral direction X and extending in the longitudinal direction Y. In one or more embodiments, the largest opening width W1 of the tail hole 70 in the lateral direction X may be smaller than a distance D5 between the center line CL1 of the main body 2 in the lateral direction X and inner edges 80S of the leakproof gathers 80 in the lateral direction X. In addition, a distance D6 between the edge 70R of the tail hole 70 on the dorsal side and the edge 30R of the absorbent core 30 on the dorsal side in the longitudinal direction Y may be longer than a distance D7 between a side edge 70S of the tail hole 70 in the lateral direction X and elastic members 40, which will be described below. The tail hole 70 is not limited to having substantially a tongue shape and may have a semicircular shape, a rectangular shape, a trapezoidal shape, a polygonal shape, or an elliptical shape.

A tongue piece 72 is formed in the main body 2. For example, the tongue piece 72 is a flap-shaped member which is formed by making the cut 50 with respect to the main body 2 and is constituted of a part of the top sheet 10 and the back sheet 20, for example. The tongue piece 72 has a shape that substantially coincides with an opening shape of the tail hole 70 and is disposed in a manner of overlapping the tail hole 70. The tongue piece 72 has a base end portion 72R coupled to the edge 70R of the tail hole 70 on the dorsal side, a distal end portion 72F positioned on a side opposite to the base end portion 72R, and side portions 72S connecting the base end portion 72R and the distal end portion 72F to each other. The distal end portion 72F is connected to the intermediate area 53 of the main body 2. On the other hand, the distal end portion 72F and the side portions 72S are not connected to the intermediate area 53 of the main body 2 and are free. The distal end portion 72F of the tongue piece 72 is directed to the ventral side in a state where the tongue piece 72 is not folded back (a state of overlapping the tail hole 70).

As illustrated in FIG. 3, the tongue piece 72 is constituted to open the tail hole 70 when it is folded back to the rear surface side Z2 with the base end portion 72R as a fold line. As described above, since the distal end portion 72F of the tongue piece 72 is directed to the ventral side, the tail is inserted into the tail hole 70, and when the tongue piece 72 is folded back to the rear surface side Z2 with the base end portion 72R as a fold line, the tongue piece 72 abuts a dorsal surface side of the tail. Due to the tongue piece 72 disposed on the dorsal surface side of the tail, adhesion of feces to the tongue piece 72 at the time of excretion is suppressed. In one or more embodiments, the distal end portion 72F and the side portions 72S of the tongue piece 72 may be temporarily tacked to the intermediate area 53 of the main body 2 via a discontinuous cut, for example, a perforated line, and the distal end portion 72F and the side portions 72S may be freed from the intermediate area 53 of the main body 2 by tearing off the tongue piece 72 along the perforated line.

Figure 4:
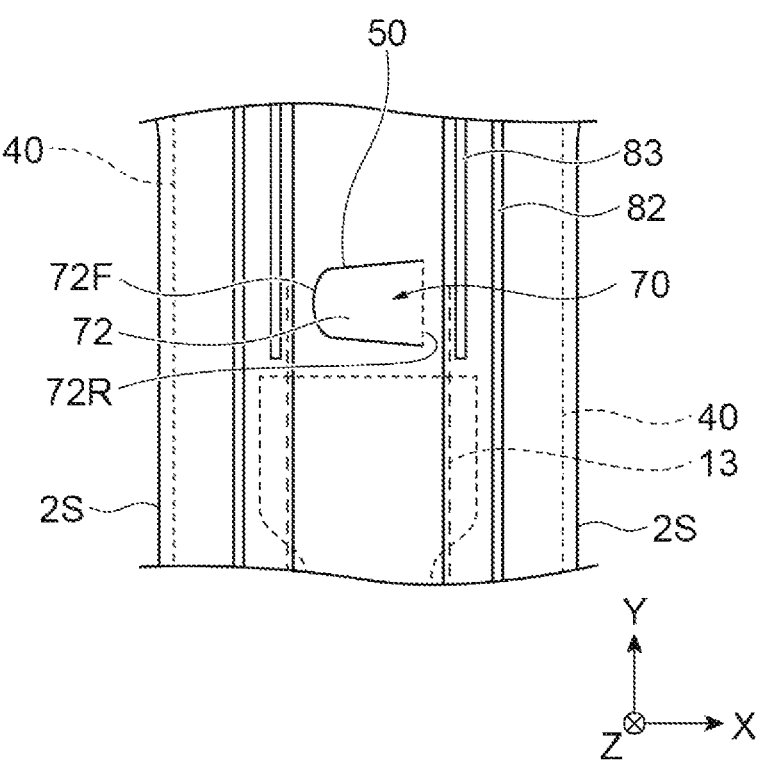
FIG. 4 is a view illustrating a modification example of a tail hole.
Figure 5:
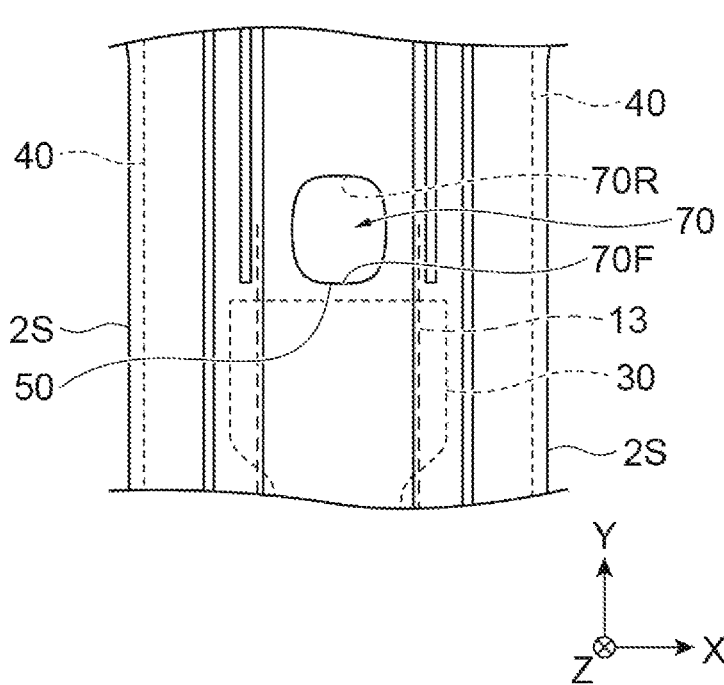
FIG. 5 is a view illustrating another modification example of the tail hole.

In addition, in one or more embodiments, as illustrated in FIG. 4, the tongue piece 72 may be formed by making the cut 50 having substantially a U-shape opening in the lateral direction X of the main body 2. The distal end portion 72F of the tongue piece 72 illustrated in FIG. 4 is directed in the lateral direction X when the tongue piece 72 is in a state of not being folded back. In the embodiments illustrated in FIG. 4, when the tail is inserted into the tail hole 70 and the tongue piece 72 is folded back to the rear surface side Z2 with the base end portion 72R as a fold line, the tongue piece 72 abuts a side portion of the tail of a pet. In addition, in one or more embodiments, as illustrated in FIG. 5, the tail hole 70 not having the tongue piece 72 may be formed by making a ring-shaped cut 50 throughout the whole circumference of an edge of the tail hole 70 and cutting out a part of the main body 2. Even in the embodiments illustrated in FIGS. 4 and 5, since the tongue piece 72 is not disposed below the anus 98 of a pet when the tail is inserted into the tail hole 70, adhesion of feces to the pet diaper 1 at the time of excretion is suppressed.

Next, the leakproof gathers 80 will be described in more detail. The leakproof gathers 80 are disposed on the outward side of the absorbent core 30 in the lateral direction X and curb leakage of urine which has been excreted to the absorbent core 30 in the lateral direction X. In one or more embodiments, the leakproof gathers 80 each include the elastic member 13 extending in the longitudinal direction Y, a standing portion 81 standing upright due to contraction of the elastic member 13, a lateral fixed portion 82 serving as a standing fulcrum of the standing portion 81 in the lateral direction X, and a vertical fixed portion 83 serving as a standing fulcrum of the standing portion 81 in the longitudinal direction Y. The standing portion 81, the lateral fixed portion 82, and the vertical fixed portion 83 of the leakproof gather 80 are constituted of the side sheet 12. The standing portion 81 is a part of the side sheet 12 not connected to the center sheet 11, and the elastic member 13 in a stretched state is disposed in the standing portion 81.

The lateral fixed portion 82 is a part of the side sheet 12 fixed to the center sheet 11 on the outward side of the standing portion 81 in the lateral direction X and serves as the standing fulcrum of the standing portion 81 in the lateral direction X. The lateral fixed portion 82 may be formed in the entire area of the main body 2 in the longitudinal direction Y at a position on the outward side in the lateral direction X with respect to the standing portion 81.

The vertical fixed portion 83 is a part of the side sheet 12 fixed to the center sheet 11 on the outward side of the standing portion 81 in the longitudinal direction Y and serves as the standing fulcrum of the standing portion 81 in the longitudinal direction Y. In one or more embodiments, the vertical fixed portion 83 includes a first vertical fixed portion 83R and a second vertical fixed portion 83F. The first vertical fixed portion 83R is formed at a position on the inward side in the lateral direction X with respect to the lateral fixed portion 82, that is, a position on the dorsal side of the absorbent core 30. More specifically, an edge 831 of the first vertical fixed portion 83R on the ventral side is disposed at a position between the edge 70F of the tail hole 70 on the ventral side and the edge 30R of the absorbent core 30 on the dorsal side. The second vertical fixed portion 83F is formed at a position on the inward side in the lateral direction X with respect to the lateral fixed portion 82, that is, a position on the ventral side from the absorbent core 30. That is, the vertical fixed portion 83 is fixed to the main body 2 at a position on the outward side from the absorbent core 30 in the longitudinal direction Y.

As described above, the standing portion 81 is disposed on the inward side in the lateral direction X with respect to the lateral fixed portion 82 and the inward side in the longitudinal direction Y with respect to the vertical fixed portion 83. The elastic member 13 stretched in the longitudinal direction Y is connected to the standing portion 81, and the main body 2 is deformed in a closing direction due to contraction of the elastic member 13 in the longitudinal direction Y. Due to this deformation, the standing portion 81 stands upright with the lateral fixed portion 82 as a fold line. In this manner, the standing portions 81 prevent leakage of urine by standing upright at positions sandwiching the absorbent core 30 therebetween in the lateral direction X.

The pet diaper 1 further includes a pair of elastic members or elastic strings (first elastic strings) 40 which can be stretched in a length direction. As illustrated in FIG. 1, the pair of elastic members 40 are disposed on the outward side in the lateral direction X from the elastic members 13 of the leakproof gathers 80. In the embodiments illustrated in FIG. 1, the elastic members 40 extend in the entire area of the main body 2 in the longitudinal direction Y. The elastic members 40 are fixed to the main body 2 in a state of being stretched in the longitudinal direction Y, thereby applying a force causing the main body 2 to be deformed in the closing direction. For example, the pair of elastic members 40 are rubber threads or flat rubbers which can contract in the length direction and are disposed along side edges 2S of the main body 2 between the top sheet 10 and the back sheet 20 of the main body 2. The pair of elastic members 40 may extend in the longitudinal direction Y in a state of sewed onto the top sheet 10 and the back sheet 20 of the main body 2.

In one or more embodiments, when the pet diaper 1 is in a stretched state, stretch ratios of the elastic members 40 may be higher than stretch ratios of the elastic members 13 of the leakproof gathers 80. A stretch ratio indicates a degree of elongation when natural lengths of the elastic members 40 or the elastic members 13 are 1. The natural lengths of the elastic members 40 or the elastic members 13 are lengths of the elastic members 40 or the elastic members 13 when no external force is applied thereto. For example, the stretch ratios of the elastic members 40 are obtained by (lengths of the elastic members 40 in a stretched state)/(lengths of the elastic members 40 in a natural state). Contractile forces of the elastic members 40 or the elastic members 13 increase as the stretch ratios are increased. By setting the stretch ratios of the elastic members 40 to be higher than the stretch ratios of the elastic members 13, the side edges 2S of the main body 2 can be brought into tight contact with a pet due to contractile forces of the elastic members 40, and occurrence of displacement in the pet diaper 1 can be suppressed even when a pet strenuously moves, for example.

In one or more embodiments, effective lengths of the elastic members 40 may be longer than effective lengths of the elastic members 13. An effective length is a length of a part of the elastic members 40 or the elastic members 13 which actually contracts. For example, in the embodiments illustrated in FIG. 1, the effective lengths of the elastic members 40 coincide with the length of the main body 2 in the longitudinal direction Y, and the effective lengths of the elastic members 13 coincide with a distance between the edge of the first vertical fixed portion 83R on the ventral side and the edge of the second vertical fixed portion 83F on the dorsal side. By setting the effective lengths of the elastic members 40 to be longer than the effective lengths of the elastic members 13, fitting properties of the pet diaper 1 can be secured due to the contractile forces of the elastic members 40 even when the elastic members 13 are cut due to strenuous movement or the like of a pet, for example.

In the embodiments illustrated in FIG. 1, the elastic members 40 extend in the entire area of the main body 2 in the longitudinal direction Y. Therefore, the elastic members 40 overlap a region extending in the lateral direction X from a region between the tail hole 70 and the absorbent core 30.

According to this constitution, due to contraction of the elastic members 40, a region between the edge 70F of the tail hole 70 on the ventral side and the edge 30R of the absorbent core 30 on the dorsal side in the main body 2 is pulled to the absorbent core 30 side and is pressed against the rump of a pet. Accordingly, fitting properties between the main body 2 and the rump of a pet are improved, and thus a gap is unlikely to be generated between the main body 2 and the rump of a pet. As a result, feces are unlikely to enter the inside of the pet diaper 1, and thus feces are unlikely to adhere to a pet.

Particularly, in the pet diaper 1, since the absorbent core 30 is not disposed in regions of the tail hole 70 and the absorbent core 30 in the main body 2, rigidities in these regions are reduced as much as that of the absorbent core 30. Therefore, since the regions of the tail hole 70 and the absorbent core 30 are flexibly deformed along the rump of a pet, a gap is less likely to be generated between the main body 2 and the rump of a pet.

Figure 6:
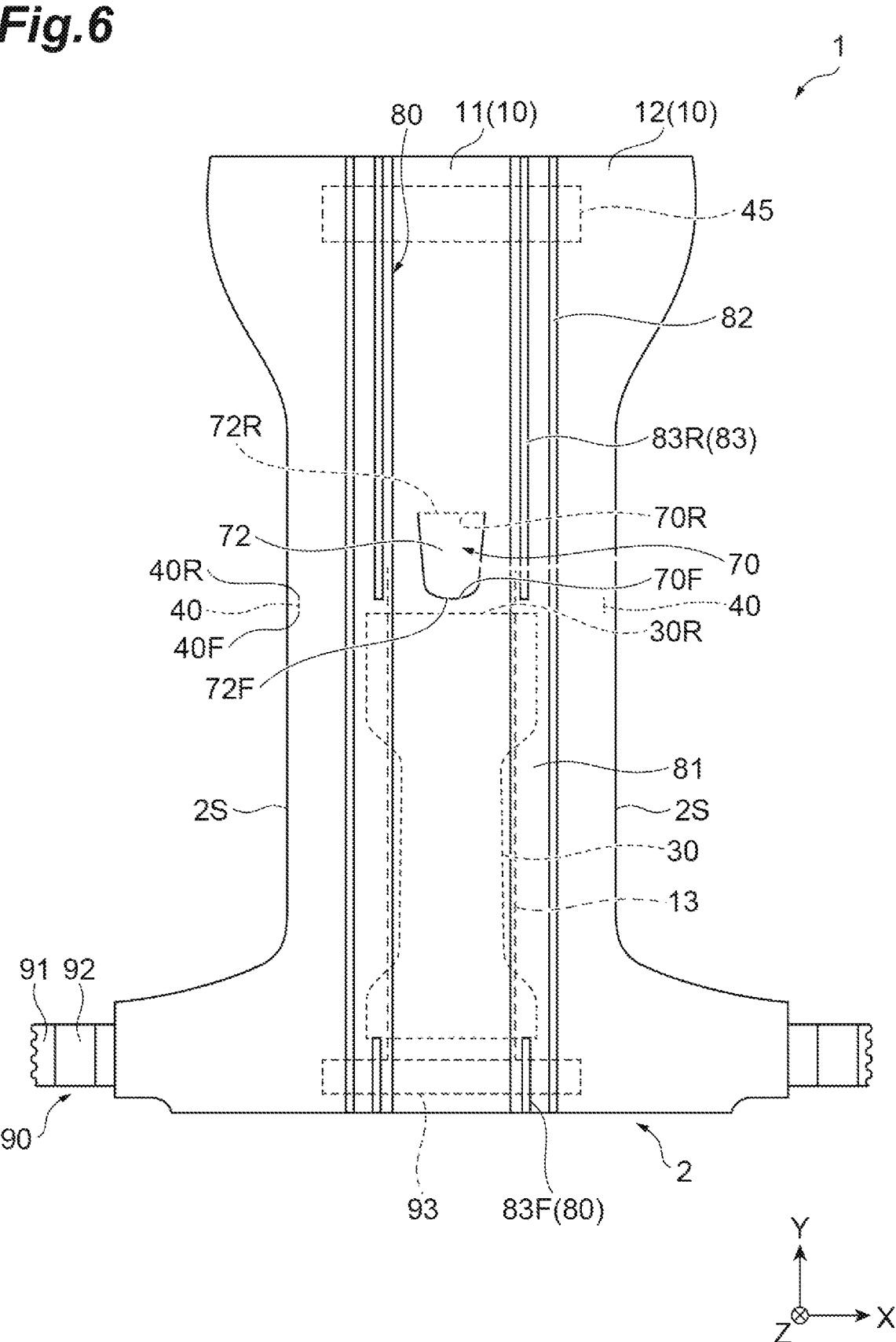
FIG. 6 is a plan view illustrating the pet diaper according to one or more embodiments.

The elastic members 40 may not extend in the entire area of the main body 2 in the longitudinal direction Y. For example, as illustrated in FIG. 6, the elastic members 40 need only extend between at least the edge 70F of the tail hole 70 on the ventral side and the edge 30R of the absorbent core 30 on the dorsal side in the longitudinal direction Y. If the elastic members 40 extend between at least the edge 70F of the tail hole 70 on the ventral side and the edge 30R of the absorbent core 30 on the dorsal side, since a region between the tail hole 70 and the absorbent core 30 in the main body 2 is pulled to the absorbent core 30 side due to the contractile forces of the elastic members 40, it is possible to prevent a gap from being likely to be generated between the main body 2 and the rump of a pet.

Figure 7:
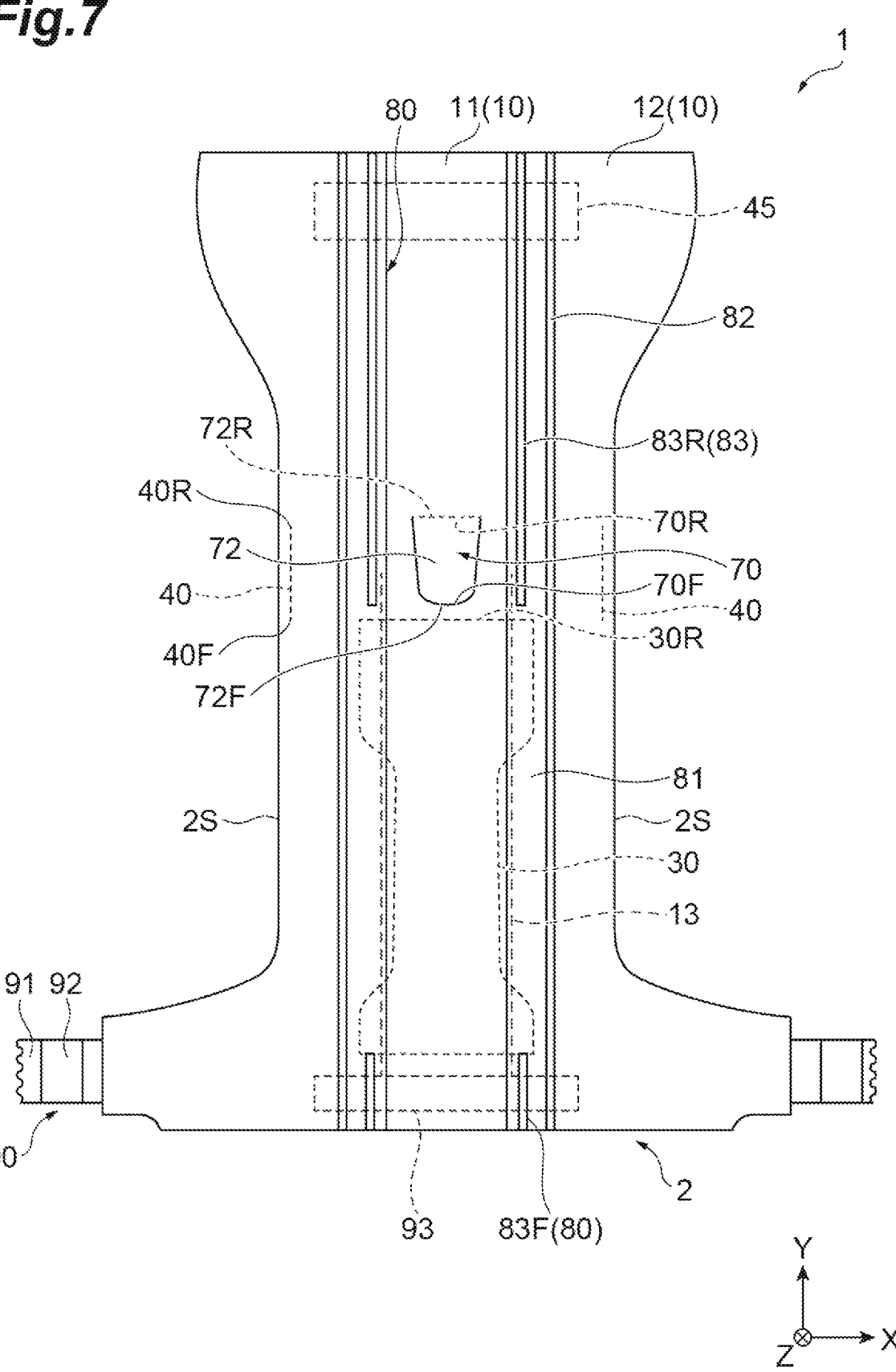
FIG. 7 is a plan view illustrating the pet diaper according to one or more embodiments.

In one or more embodiments, the elastic members 40 may extend beyond a central position of the tail hole 70 in the longitudinal direction Y. For example, in the embodiments illustrated in FIG. 7, in the longitudinal direction Y, edges 40R of the elastic members 40 on the dorsal side are disposed between the edge 70R of the tail hole 70 on the dorsal side and the central position of the tail hole 70, and edges 40F of the elastic members 40 on the ventral side are disposed at positions which coincide with the edge 30R of the absorbent core 30 on the dorsal side. In one or more embodiments, since a region on the outward side of the tail hole 70 in the lateral direction X is pressed against the rump of a pet due to contraction of the elastic members 40, a gap is unlikely to be generated between the side edge 70S of the tail hole 70 in the lateral direction X and the rump of a pet.

Figure 8:
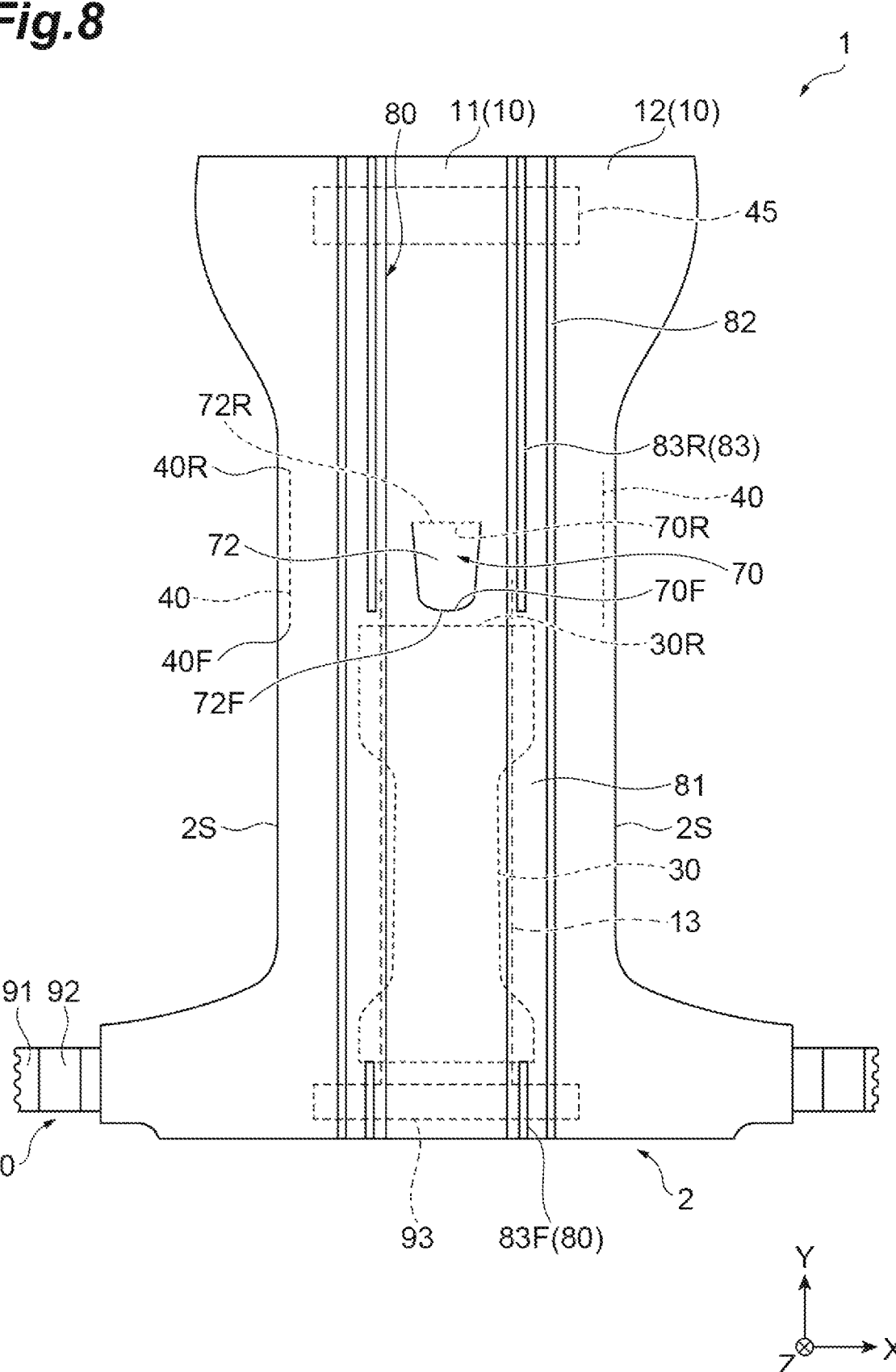
FIG. 8 is a plan view illustrating the pet diaper according to one or more embodiments.

In one or more embodiments, the elastic members 40 may extend beyond in the edge 70R of the tail hole 70 on the dorsal side in the longitudinal direction. For example, in the embodiments illustrated in FIG. 8, in the longitudinal direction Y, the edges 40R of the elastic members 40 on the dorsal side are disposed between the edge 70R of the tail hole 70 on the dorsal side and the target portion 45, and the edges 40F of the elastic members 40 on the ventral side are disposed at positions which coincide with the edge 30R of the absorbent core 30 on the dorsal side in the longitudinal direction Y. In one or more embodiments, since a region in the main body 2 on the dorsal side of the tail hole 70 is pressed against the dorsal portion of a pet due to contraction of the elastic members 40, fitting properties of the pet diaper 1 are improved.

Figure 9:
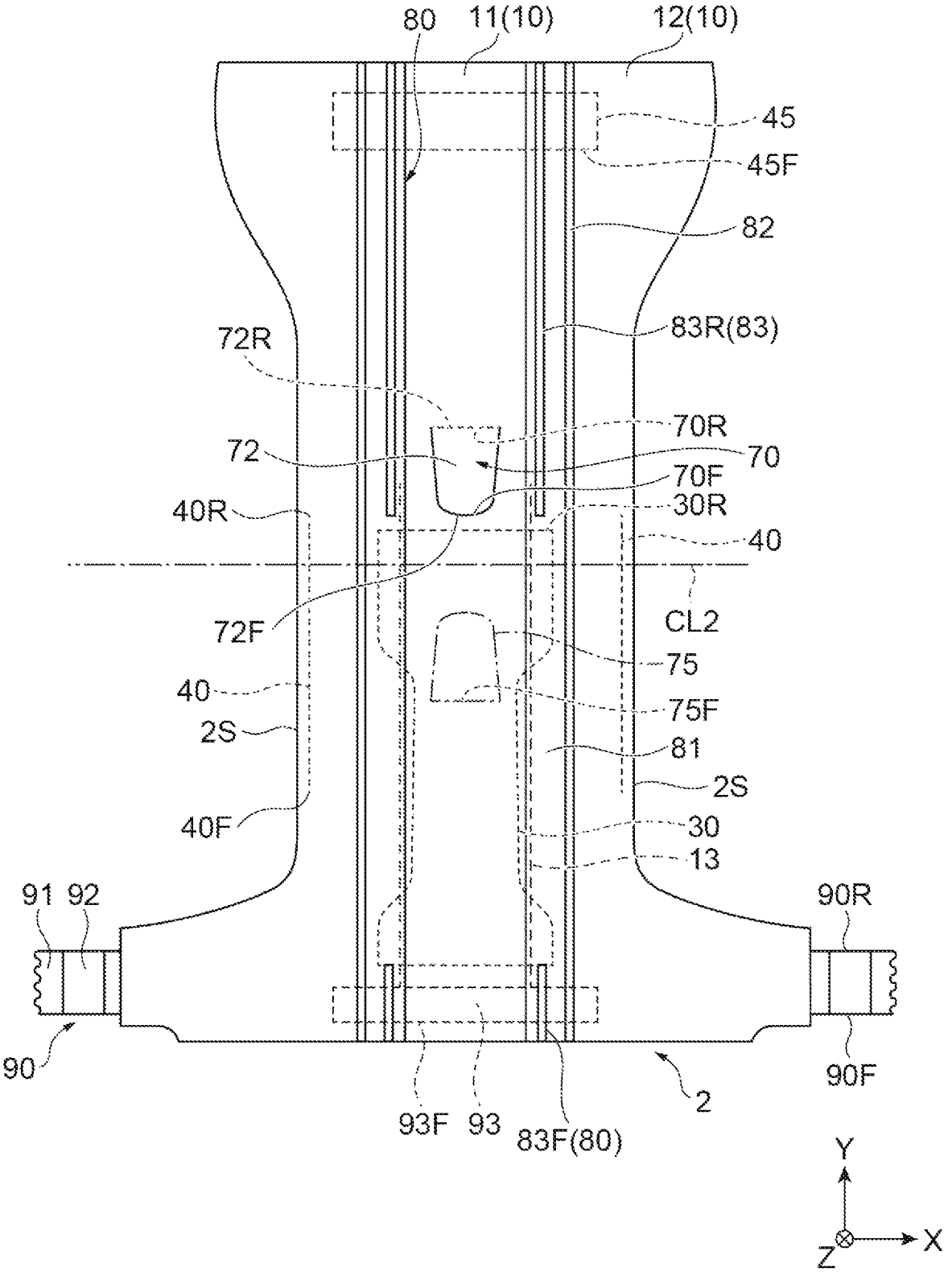
FIG. 9 is a plan view illustrating the pet diaper according to one or more embodiments.

In one or more embodiments, when a virtual tail hole 75 is set at a position line-symmetrical to the tail hole 70 with respect to the center line CL2 in the longitudinal direction Y, the elastic members 40 may extend beyond an edge 75F of the virtual tail hole 75 on the ventral side. For example, in the embodiments illustrated in FIG. 9, the edges 40R of the elastic members 40 on the dorsal side are disposed at positions which coincide with the edge 70F of the tail hole 70 on the ventral side in the longitudinal direction Y, and the edges 40F of the elastic members 40 on the ventral side are disposed between the edge 75F of the virtual tail hole 75 on the ventral side and the fastening tabs 90 in the longitudinal direction Y. In one or more embodiments, since the elastic member 40 extends to the ventral side over the center line CL2, a region in the main body 2 on the ventral side is pressed against the ventral portion of a pet due to contraction of the elastic members 40, and thus fitting properties of the pet diaper 1 are improved.

Figure 10:
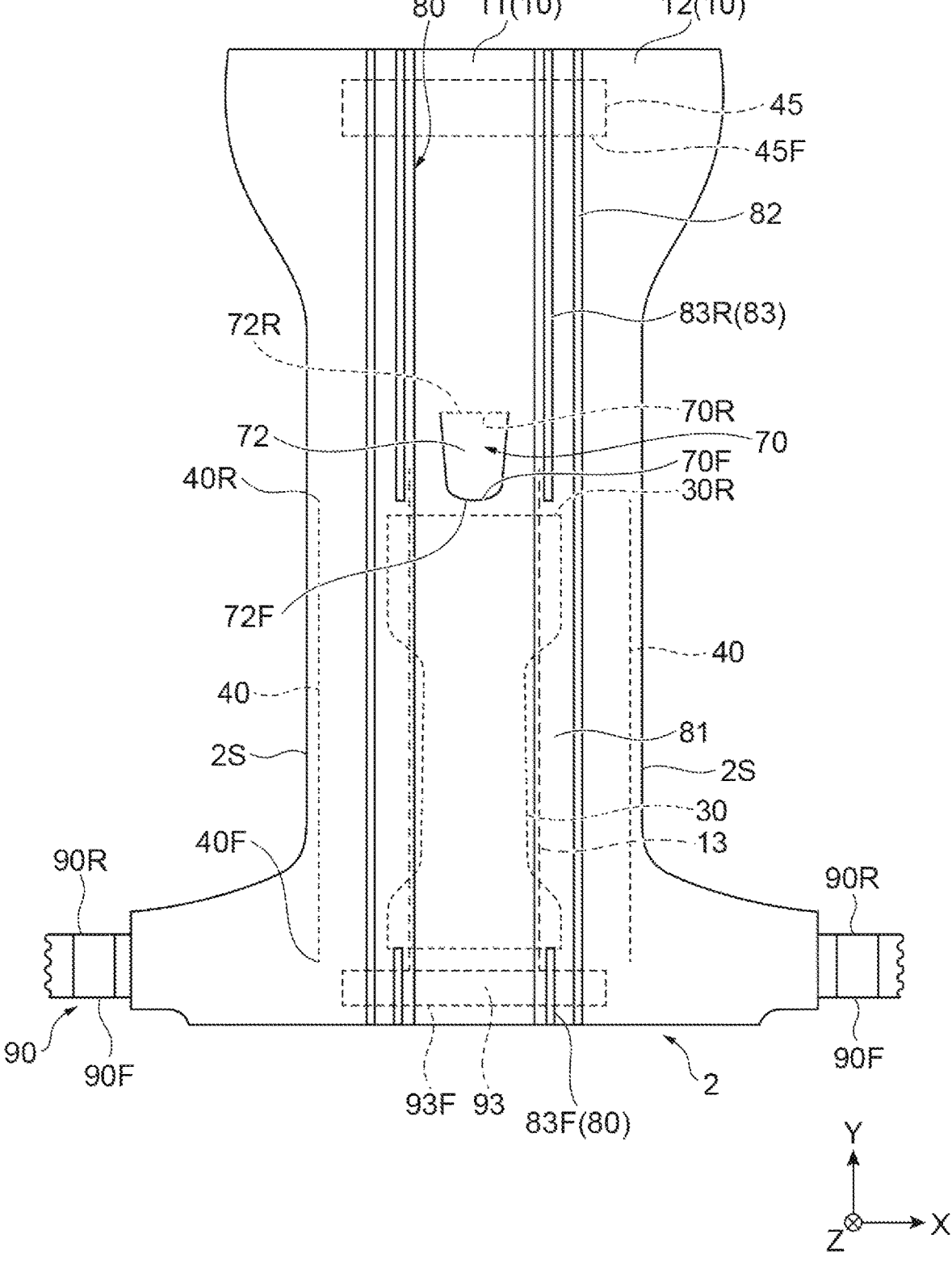
FIG. 10 is a plan view illustrating the pet diaper according to one or more embodiments.

In one or more embodiments, the elastic members 40 may extend beyond the edges 90R of the pair of fastening tabs 90 on the dorsal side in the longitudinal direction Y. For example, in the embodiments illustrated in FIG. 10, the edges 40R of the elastic members 40 on the dorsal side are disposed at positions which coincide with the edge 70F of the tail hole 70 on the ventral side in the longitudinal direction Y, and the edges 40F of the elastic members 40 on the ventral side are disposed between the edges 90R of the fastening tabs 90 on the dorsal side in the longitudinal direction Y and edges 90F of the fastening tabs 90 on the ventral side. In one or more embodiments, since the elastic members 40 extend beyond the edges 90R of the pair of fastening tabs 90 on the dorsal side, the elastic members 40 are stretched to the ventral side due to tensile forces pulling up the pair of fastening tabs 90 for engagement with the target portion 45, and the main body 2 is pressed against the rump of a pet due to the contractile forces of the elastic members 40. Therefore, fitting properties of the pet diaper 1 are improved.

Figure 11:
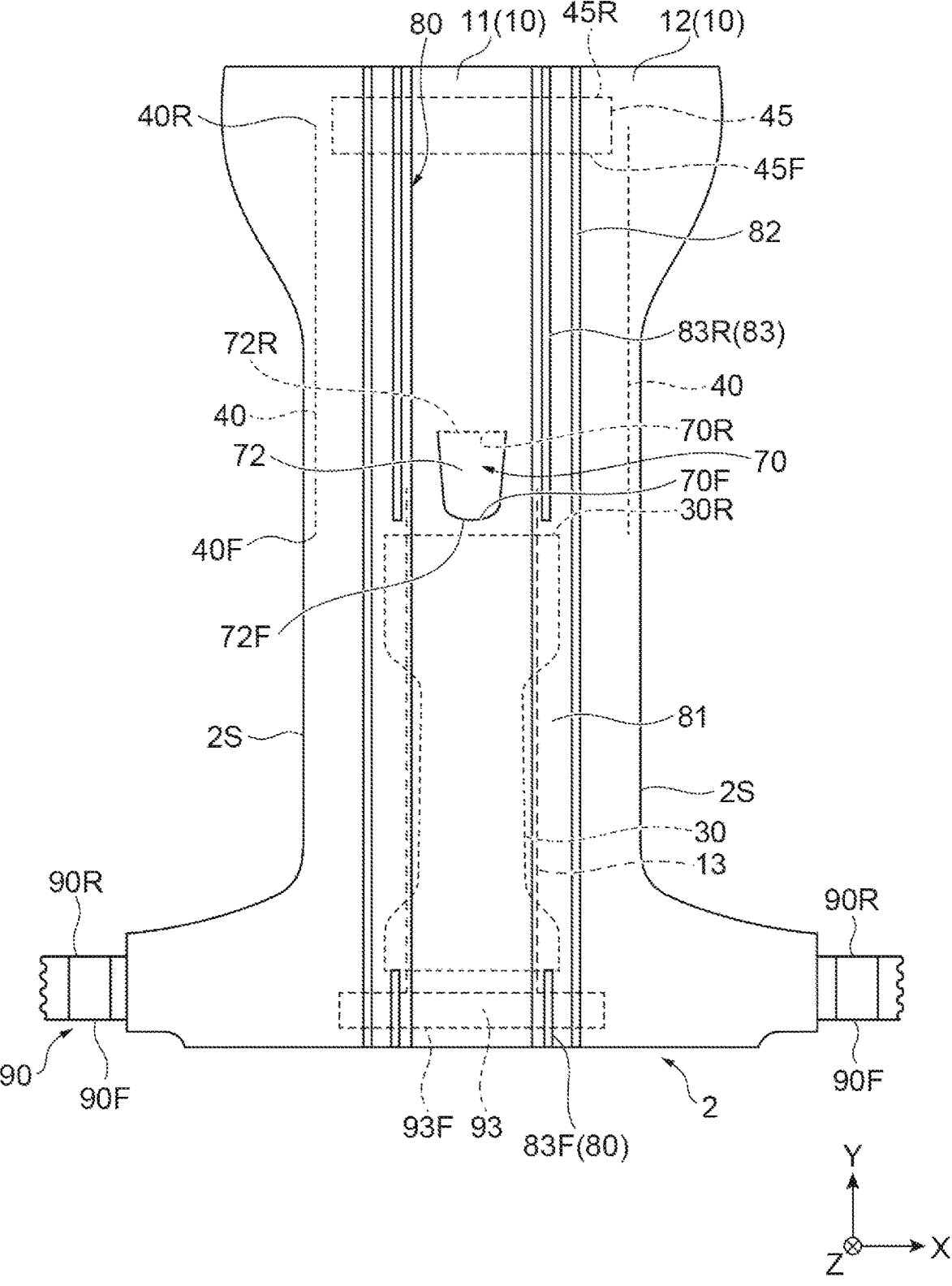
FIG. 11 is a plan view illustrating the pet diaper according to one or more embodiments.

In one or more embodiments, the elastic members 40 may extend beyond the edge 45F of the target portion 45 on the ventral side in the longitudinal direction. For example, in the embodiments illustrated in FIG. 11, the edges 40R of the elastic members 40 on the dorsal side are disposed between the edge 45F of the target portion 45 on the ventral side and an edge 45R of the target portion 45 on the dorsal side in the longitudinal direction Y, and the edges 40F of the elastic members 40 on the ventral side are disposed at positions which coincide with the edge 30R of the absorbent core 30 on the dorsal side. Generally, a pet such as a dog or a cat adopts a posture with a protruding rump and a rounded dorsal portion at the time of defecation. In one or more embodiments, since the elastic members 40 extend beyond the edge 45F of the target portion 45 on the ventral side, the elastic members 40 are stretched when a pet has the rounded dorsal portion at the time of defecation, and the main body 2 is pressed against the dorsal portion of a pet due to the contractile forces of the elastic members 40. Therefore, fitting properties of the pet diaper 1 are improved.

Figure 12:
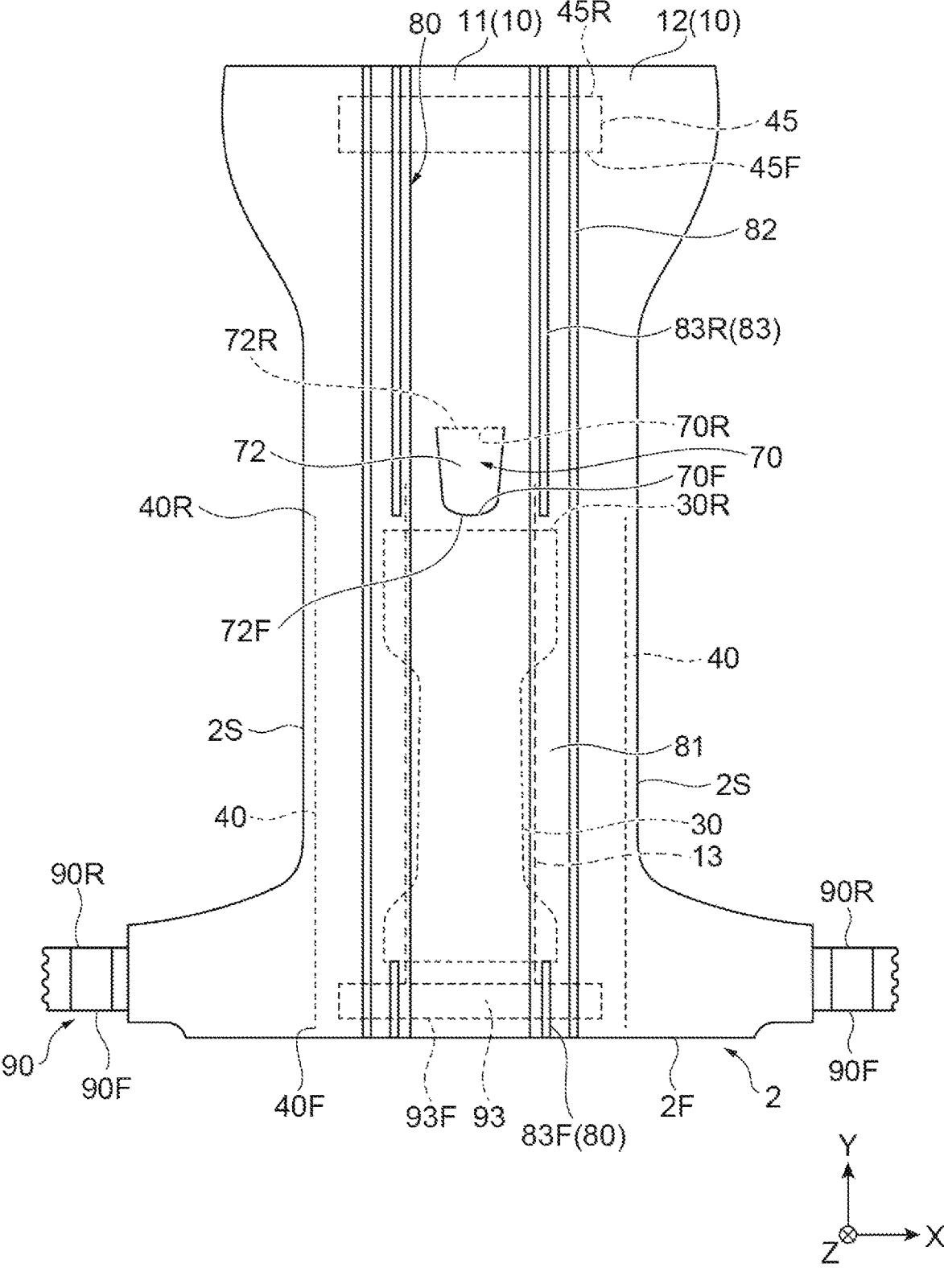
FIG. 12 is a plan view illustrating the pet diaper according to one or more embodiments.

In one or more embodiments, the elastic members 40 may extend beyond an edge 93F of the waist gather 93 on the dorsal side. For example, in the embodiments illustrated in FIG. 12, the edges 40R of the elastic members 40 on the dorsal side are disposed at positions which coincide with the edge 70F of the tail hole 70 on the ventral side, and the edges 40F of the elastic members 40 on the ventral side are disposed between the waist gather 93 and the ventral side edge 2F in the longitudinal direction Y. Since the elastic members 40 extend beyond the edge 93F of the waist gather 93 on the dorsal side, the elastic members 40 are stretched to the ventral side due to contraction of the waist gather. For this reason, the main body 2 is pressed against the ventral portion of a pet due to contraction of the elastic members 40, and thus fitting properties of the pet diaper 1 are improved.

Figure 13:
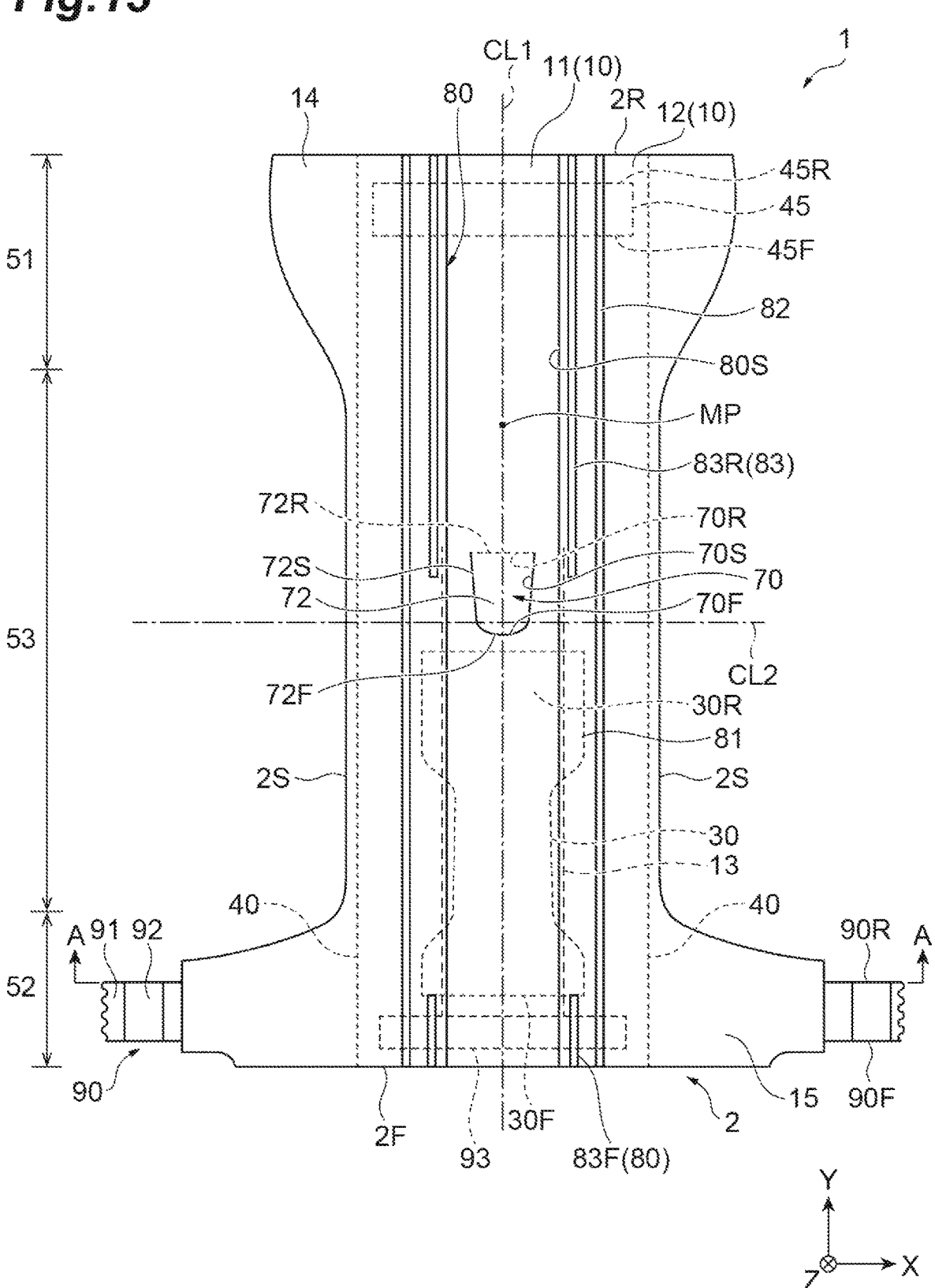
FIG. 13 is a plan view illustrating the pet diaper according to one or more embodiments.

In the embodiments illustrated in FIG. 1, the edge 70F of the tail hole 70 on the ventral side is disposed on the dorsal side from the center line CL2 of the main body 2 in the longitudinal direction Y. However, in one or more embodiments, the edge 70F of the tail hole 70 on the ventral side may be disposed on the ventral side from the center line CL2 of the main body 2 in the longitudinal direction Y. For example, in the embodiments illustrated in FIG. 13, the edge 70R of the tail hole 70 on the dorsal side is disposed on the dorsal side from the center line CL2, and the edge 70F of the tail hole 70 on the ventral side is disposed on the ventral side from the center line CL2. Since the tail hole 70 is disposed substantially in a horizontal manner when a pet adopts a sitting posture by setting the position of the tail hole 70 in this manner, feces can more reliably pass therethrough.

FIG. 3 is a view illustrating a state where the pet diaper 1 is worn by a pet. When the pet diaper 1 is worn by a pet, first, the anus 98 of the pet is exposed from the tail hole 70 by causing the tail of the pet to pass through the tail hole 70 and come out to the rear surface side Z2 of the diaper. At this time, the tongue piece 72 is folded back to the rear surface side Z2 with the base end portion 72R as a fold line, and therefore the tongue piece 72 abuts the dorsal surface side of the tail. Next, the ventral side edge 2F of the main body 2 is brought into contact with the abdomen of the pet. Further, while a part in the vicinity of the center line CL2 of the main body 2 in the longitudinal direction Y is brought into contact with the urination opening of the pet, the dorsal side edge 2R of the main body 2 is brought into contact with the dorsal portion of the pet. Next, the pair of fastening tabs 90 are pulled to the back side of the pet in the girth direction, and the pair of fastening tabs 90 are interlocked with an outer surface of the target portion 45 of the main body 2. Accordingly, as illustrated in FIG. 3, the pet diaper 1 is worn such that the abdomen, the back, and the crotch of the pet are covered.

As described above, in the pet diaper 1 according to the embodiments described above, since the anus 98 of a pet is exposed from the tail hole 70 of the main body 2 by the tail hole 70, while urine of the pet is received by the pet diaper 1, feces of the pet can pass through the tail hole 70 and be discharged to the outside. Particularly, in the pet diaper 1, since the tail hole 70 has a vertically elongated shape, when the pet diaper 1 is worn by a pet, the anus 98 of the pet can be reliably exposed from the main body 2. In addition, by disposing the edge 70R of the tail hole 70 on the dorsal side on the ventral side from the middle point MP between the center line CL2 of the main body 2 and the edge 45F of the target portion 45 on the ventral side in the longitudinal direction Y, when the pet diaper 1 is worn, the edge 70R of the tail hole 70 on the dorsal side can reliably abut the dorsal portion of the tail. Therefore, displacement of the pet diaper 1 is suppressed, and feces can be discharged to the outside of the pet diaper 1 while leakage of urine is prevented. In the pet diaper 1, a feces bag for collecting feces discharged from the tail hole 70 is not attached.

Incidentally, if a gap is present between the edge of the tail hole 70 and the rump of a pet, there is concern that feces may enter the inside of the pet diaper 1 through the gap and adhere to the pet. Particularly, in a case of loose feces, when a slight gap is simply present between the edge of the tail hole 70 and the rump of a pet, the loose feces may enter the inside of the pet diaper 1 through the gap and spread inside the pet diaper 1. In this case, it takes time and effort to wash away feces which have spread and adhered to the pet using a shower or the like. In contrast, in the pet diaper 1, since a region between the tail hole 70 and the absorbent core 30 in the main body 2 is pressed against the rump of a pet due to contraction of the elastic members 40, a gap is unlikely to be generated between the edge of the tail hole 70 and the rump of a pet. Therefore, a situation in which feces enter the inside of the pet diaper 1 through the gap and the feces adhere to a pet is suppressed.

Figure 14:
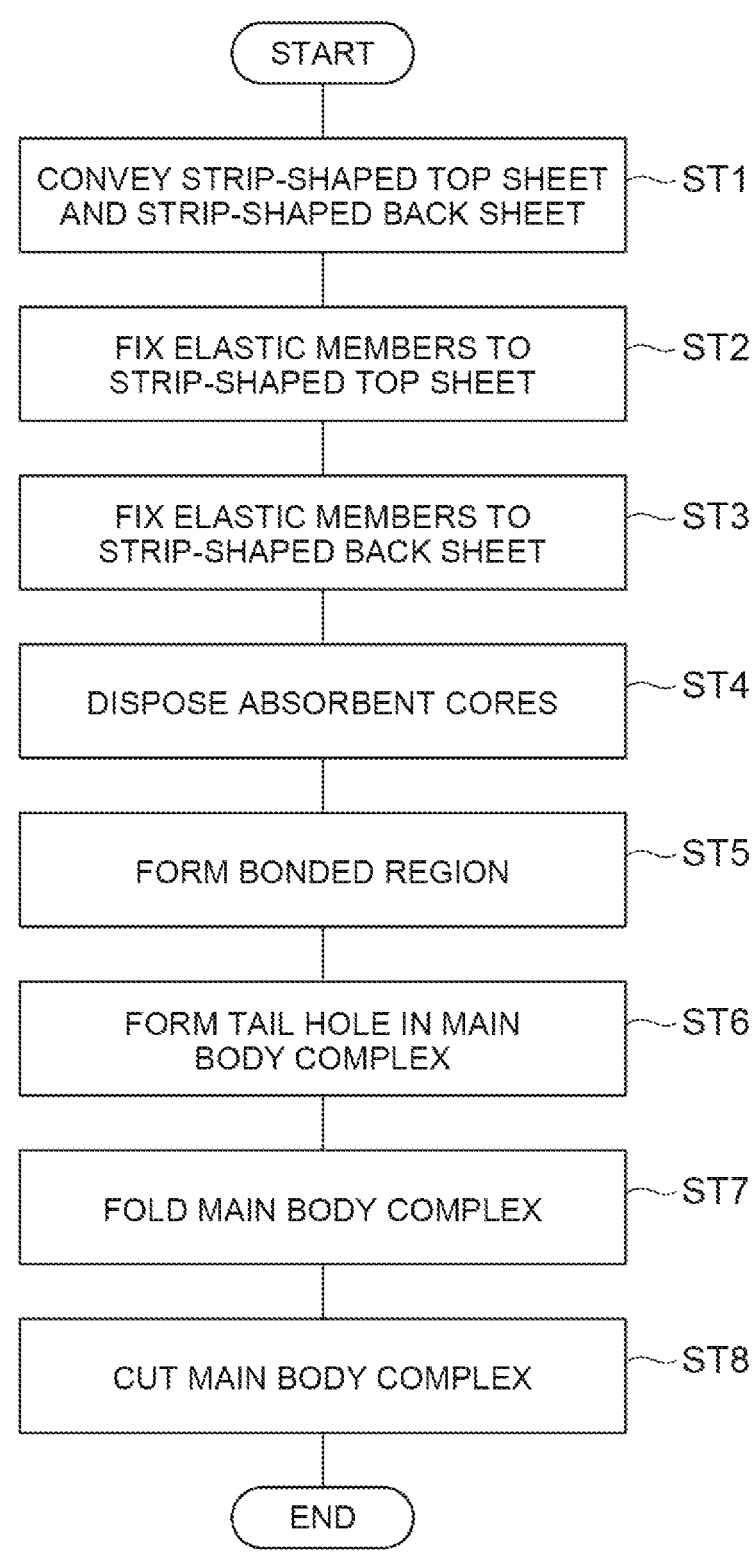
FIG. 14 is a flowchart showing a method for manufacturing a pet diaper according to one or more embodiments.
Figure 15:
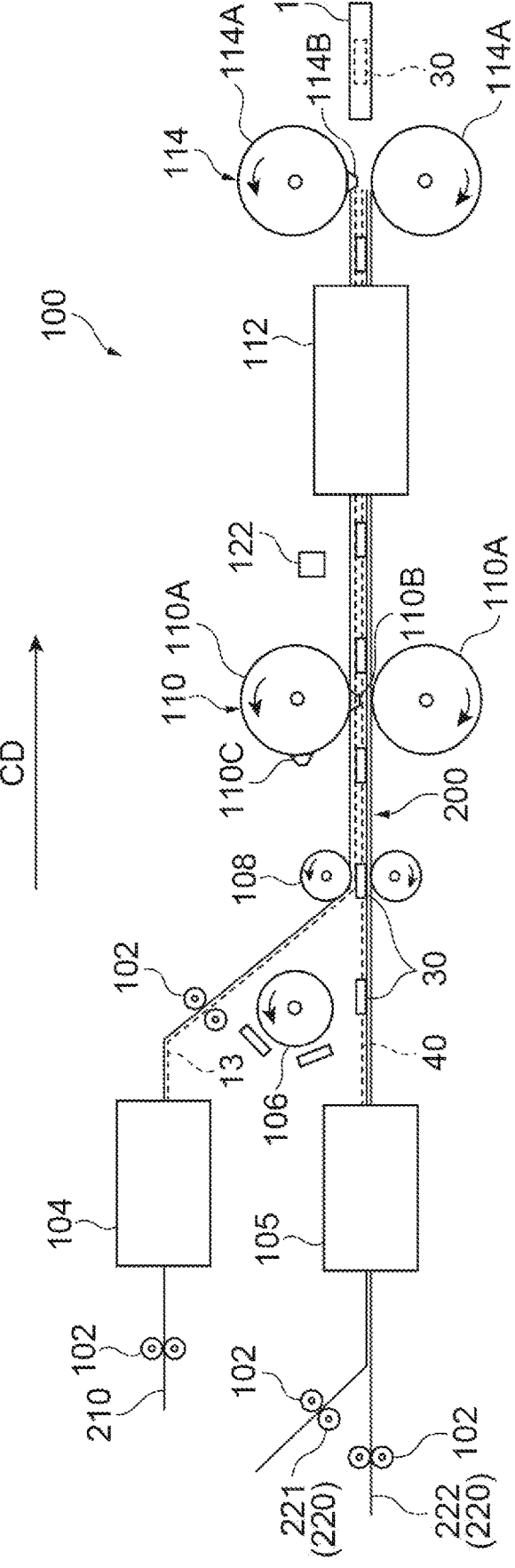
FIG. 15 is a view schematically illustrating an example of a manufacturing apparatus in which the method for manufacturing a pet diaper is applied.

Next, with reference to FIGS. 14 and 15, a method for manufacturing the pet diaper 1 described above will be described. FIG. 14 is a flowchart showing a method for manufacturing a pet diaper according to one or more embodiments. FIG. 15 is a view schematically illustrating an example of a manufacturing apparatus in which the method for manufacturing a pet diaper according to one or more embodiments is applied. In this method for manufacturing a pet diaper, the pet diapers 1 described above are continuously manufactured by executing each of steps, which will be described below. In the following description, the terms "upstream" and "downstream" are used based on a conveyance direction of a conveyance direction CD, which will be described below.

As illustrated in FIG. 15, a manufacturing apparatus 100 includes a conveyance roller 102, elastic member supply devices (i.e., elastic string supply devices) 104 and 105, an absorbent core supply device 106, a bonding device 108, a tail hole forming device 110, a folding device 112, and a cutting device 114.

In the method for manufacturing a pet diaper according to one or more embodiments, first, the conveyance roller 102 conveys a strip-shaped top sheet (or belt-shaped top sheet) 210 that is a strip-shaped sheet member in which the top sheets 10 of the pet diaper 1 are connected in the longitudinal direction Y and a strip-shaped back sheet (or belt-shaped back sheet) 220 that is a strip-shaped or belt-shaped sheet member in which the back sheets 20 of the pet diaper 1 are connected in the longitudinal direction in the conveyance direction CD (Step ST1). The conveyance direction CD in which the strip-shaped top sheet 210 and the strip-shaped back sheet 220 are conveyed is a direction along the longitudinal direction Y of the pet diaper 1. A plurality of pairs of fastening tabs 90 disposed with a predetermined interval therebetween in the conveyance direction CD may be formed in the strip-shaped top sheet 210.

The strip-shaped back sheet 220 includes a liquid-impermeable strip-shaped back film (or liquid-impermeable belt-shaped back film) 221 constituted of the back films 21 connected in the longitudinal direction Y, and a strip-shaped back non-woven fabric (or belt-shaped back non-woven fabric) 222 constituted of the back non-woven fabrics 22 connected in the longitudinal direction Y. When the strip-shaped top sheet 210 and the strip-shaped back sheet 220 are stuck together, in the strip-shaped back sheet 220, the liquid-impermeable strip-shaped back film 221 constituted of the back films 21 connected in the longitudinal direction Y is disposed between the strip-shaped back non-woven fabric 222 and the strip-shaped top sheet 210. As will be described below, when the strip-shaped top sheet 210 and the strip-shaped back sheet 220 are cut such that the length in the longitudinal direction Y becomes a predetermined dimension by the cutting device 114, the top sheet 10 and the back sheet 20 are respectively formed from the strip-shaped top sheet 210 and the strip-shaped back sheet 220. The target portions 45 disposed with a predetermined interval therebetween in the conveyance direction CD and engaged with the pair of fastening tabs 90 may be formed in the strip-shaped back sheet 220.

Next, the elastic member supply device 104 fixes the pair of elastic members 13 to the strip-shaped top sheet 210 (Step ST2). The pair of elastic members 13 are fixed to the strip-shaped top sheet 210 in the conveyance direction CD, that is, in a state of being stretched in the longitudinal direction Y. Next, the elastic member supply device 105 fixes the pair of elastic members 40 to the strip-shaped back sheet 220 (Step ST3). The pair of elastic members 40 are fixed to the strip-shaped back sheet 220 in the conveyance direction CD, that is, in a state of being stretched in the longitudinal direction Y. The strip-shaped top sheet 210 having the pair of elastic members 13 fixed thereto and the strip-shaped back sheet 220 having the pair of elastic members 40 fixed thereto are conveyed to the downstream side in the conveyance direction CD.

Next, the absorbent core supply device 106 disposes a plurality of absorbent cores 30 on the strip-shaped back sheet 220 (Step ST4). The plurality of absorbent cores 30 are disposed on the strip-shaped back sheet 220 with a predetermined interval therebetween in the conveyance direction CD. Next, in a state in which the strip-shaped back sheet 220, the plurality of absorbent cores 30, and the strip-shaped top sheet 210 are sequentially laminated, the bonding device 108 forms a bonded region R1 using a hot-melt adhesive (HMA), for example, and bonds the strip-shaped back sheet 220 and the strip-shaped top sheet 210 to each other (Step ST5). Accordingly, a main body complex 200 including the strip-shaped top sheet 210, the strip-shaped back sheet 220, and the plurality of absorbent cores 30 arrayed between the strip-shaped top sheet 210 and the strip-shaped back sheet 220 with a predetermined interval in the longitudinal direction Y is formed. The formed main body complex 200 is conveyed to the downstream side in the conveyance direction CD.

Figure 16:
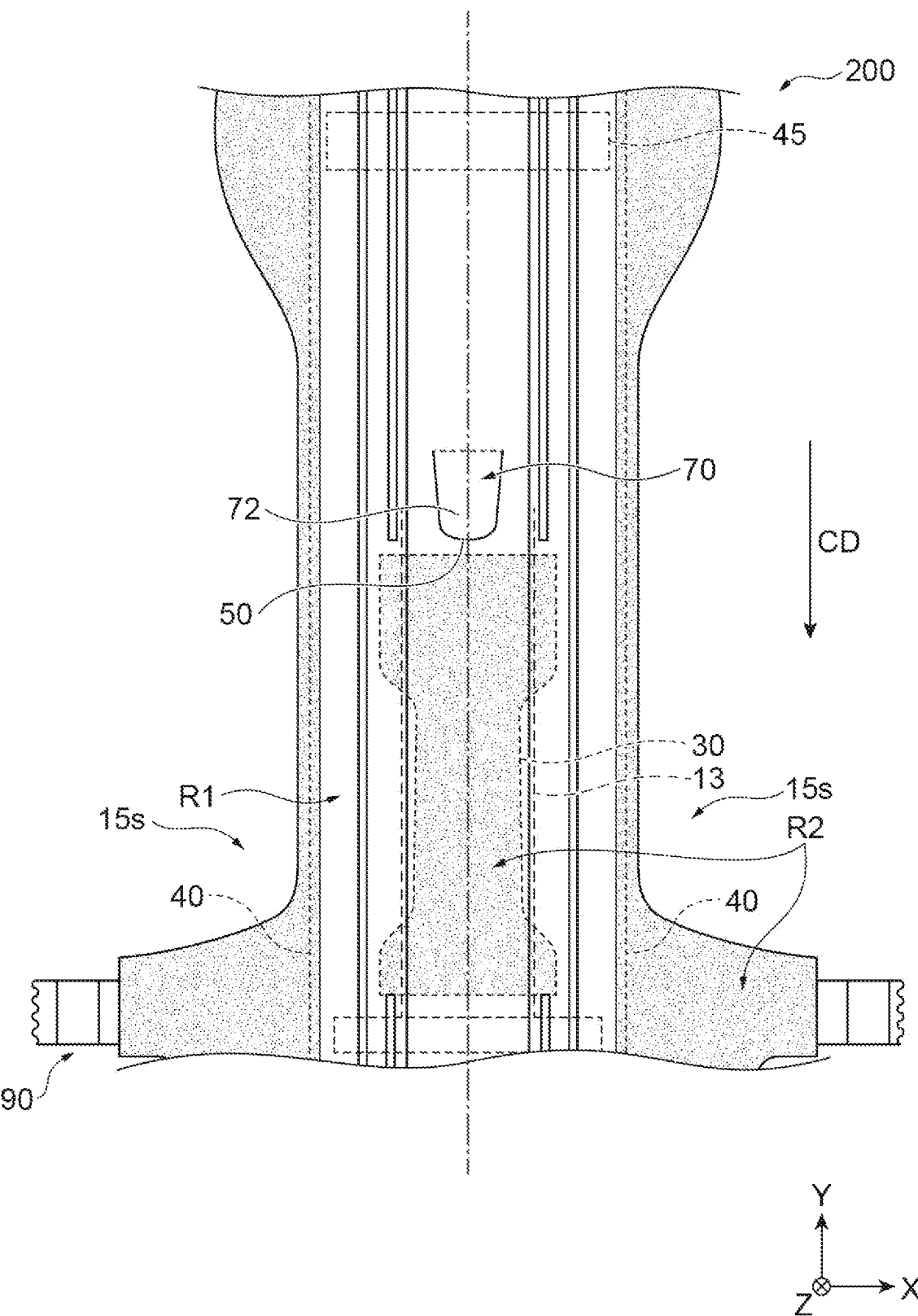
FIG. 16 is a plan view schematically illustrating a part of a main body complex.

FIG. 16 is a plan view schematically illustrating a part of the main body complex 200. As illustrated in FIG. 16, the main body complex 200 includes the bonded region R1 and a non-bonded region R2. In FIG. 16, the whitened part corresponds to the bonded region R1, and the hatched part corresponds to the non-bonded region R2. The bonded region R1 is a region in which the strip-shaped top sheet 210 and the strip-shaped back film 221 are directly bonded to each other by the bonding device 108. The non-bonded region R2 is a region in which the strip-shaped top sheet 210 and the strip-shaped back film 221 are not directly bonded to each other. Specifically, the non-bonded region R2 is a region in which the absorbent core 30 is interposed between the strip-shaped top sheet 210 and the strip-shaped back film 221 and is a region in which the strip-shaped top sheet 210 and the strip-shaped back non-woven fabric 222 are bonded to each other.

Next, the tail hole forming device 110 forms the tail hole 70 in the main body complex 200 at a position on the downstream side of the bonding device 108 (Step ST6). As illustrated in FIG. 15, the tail hole forming device 110 includes a pair of rotatable rollers 110A, a cutter 110B for forming the tail hole 70, and a cutter 110C for forming a pair of leg opening portions 15$s$. The cutter 110B is attached to an outer circumferential surface of one roller 110A of the pair of rollers 110A and has substantially a U-shaped blade edge. The cutter 110B makes the cut 50 which opens in a direction opposite to the conveyance direction CD (upstream side) with respect to the main body complex 200 passing through the pair of rollers 110A therebetween and lies along a substantially U-shaped cutting line, and forms the tail hole 70 (Step ST6). In other words, the cut 50 has a substantially U-shape protruding toward the downstream side in the conveyance direction CD. As illustrated in FIG. 16, the tail hole 70 is formed into the main body complex 200 at a position between the absorbent core 30 and the target portion 45 in the longitudinal direction Y and a position between the pair of elastic members 40 in the lateral direction X.

The tongue piece 72 having a tongue shape is formed by forming the cut 50 having substantially a U-shape. The distal end portion 72F of the tongue piece 72 is directed to the downstream side in the conveyance direction CD when the tongue piece 72 is in a state of not being folded back. The tail hole 70 opens when this tongue piece 72 is folded back to the rear surface side.

In one or more embodiments, in Step ST6, the tail hole 70 may be formed by making a substantially U-shaped cut opening in the lateral direction X (a direction perpendicular to the conveyance direction CD). In other words, the tail hole forming device 110 forms a substantially U-shaped cut protruding toward the lateral direction X. Accordingly, as illustrated in FIG. 4, when the tongue piece 72 is in a state of not being folded back, the tongue piece 72 in which the distal end portion 72F is directed in the lateral direction X is formed. The tail hole 70 opens when this tongue piece 72 is folded back to the rear surface side.

In one or more embodiments, in Step ST6, the tail hole 70 may be formed by making a cut along a ring-shaped cutting line. Here, a ring-shaped cutting line denotes a line along which a part of the main body complex 200 is to be cut out throughout the circumference, and a planar shape thereof is not limited to a toric shape and includes an arbitrary annular shape such as a rectangular ring shape or a polygonal ring shape. By making a cut along a cutting line having a planar ring shape and cutting out a part of the main body complex 200, as illustrated in FIG. 5, the tail hole 70 which does not have the tongue piece 72 is formed.

In one or more embodiments, the tail hole 70 is formed in the bonded region R1 of the main body complex 200. Since the bonded region R1 is a region in which the strip-shaped top sheet 210 and the strip-shaped back film 221 are directly bonded to each other, creases are unlikely to be generated in the main body complex 200 when the cut 50 is formed, and a neat continuous tail hole 70 having less distortion can be formed.

The cutter 110B forms parts corresponds to the pair of extending portions 14 and the pair of extending portions 15 in the main body complex 200 by cutting parts of both side portions of the main body complex 200 and forms the pair of leg opening portions 15s for allowing the hind legs of a pet to pass therethrough. The pair of leg opening portions 15s may be formed at the same time together with the tail hole 70 or may be formed after the tail hole 70 is formed and before the main body complex 200 is folded by the folding device 112. The main body complex 200 having the tail hole 70 and the pair of leg opening portions 15s formed therein is conveyed to the downstream side in the conveyance direction CD.

A tail hole sensor 122 may be provided on the downstream side of the tail hole forming device 110. For example, the tail hole sensor 122 determines whether or not the tail hole 70 is formed at an appropriate position in the main body complex 200 by capturing an image of a region having the tail hole 70 of the main body complex 200 formed therein and executing image recognition processing with respect to the captured image. When it is determined that the tail hole 70 is not formed in the main body complex 200 by the tail hole sensor 122, the tail hole sensor 122 notifies an operator of the manufacturing apparatus 100 of information indicating that there is a problem in the tail hole 70.

Next, the folding device 112 folds the pair of extending portions 14 and the pair of extending portions 15 to the inward side of the main body complex 200 (Step ST7). Next, the cutting device 114 divides the main body complex 200 into a plurality of pet diapers 1 by cutting the main body complex 200 in the lateral direction X. As illustrated in FIG. 15, the cutting device 114 includes a pair of rotatable rollers 114A and a cutter 114B for cutting the main body complex 200. The cutter 114B is attached to an outer circumferential surface of one roller 114A of the pair of rollers 114A and extends in an axial direction of the rollers 114A. The main body complex 200 conveyed by the pair of rollers 114A is cut together with the pair of elastic members 13 and the pair of elastic members 40, and the main body complex 200 is divided into a plurality of pet diapers 1. As a result, a plurality of pet diapers 1 are manufactured.

When the main body complex 200 is cut, the pet diaper 1 contracts in the longitudinal direction Y due to contractile forces of the pair of elastic members 40. It is not easy to form a neat continuous tail hole 70 having no distortion in a contracted pet diaper 1 in this manner. Particularly, when the cutting line of the cut 50 has substantially a U-shape opening in a direction opposite to the conveyance direction CD, substantially a U-shape opening in the lateral direction X, or a ring shape, since an area of a starting point (or a fold line) of the cut becomes relatively wider, a shearing force applied to the pet diaper 1 is dispersed, and thus a distorted tail hole 70 or a discontinuous tail hole 70 having a broken cut is likely to be formed. In contrast, in the method for manufacturing the pet diaper 1 described above, since the main body complex 200 is cut in the lateral direction X by the cutting device 114 together with the pair of elastic members 40 after the tail hole 70 is formed by the tail hole forming device 110, a neat tail hole 70 can be formed.

Hereinabove, pet diapers according to various embodiments and the method for manufacturing a pet diaper have been described, but the present invention is not limited to the embodiments described above and various modification forms can be constituted within a range not changing the gist of the invention. That is, it should be noted that the embodiments described above are for exemplary description and are not intended to limit the scope of the present invention. The various embodiments described above can be combined within a range having no contradiction.

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

REFERENCE SIGNS LIST

1 Pet diaper
2 Main body
2S Side edge
10 Top sheet
13 Elastic member
20 Back sheet
30 Absorbent core
40 Elastic member
45 Target portion
70 Tail hole
72 Tongue piece
72F Distal end portion
72R Base end portion 75 Virtual tail hole
80 Leakproof gather
81 Standing portion
83 Vertical fixed portion
90 Fastening tab
93 Waist gather
98 Anus
CL1, CL2 Center line
MP Middle point
W1, W2 Largest opening width

What is claimed is:

1. A pet diaper configured to extend in a lateral direction along a waist of a pet and in a longitudinal direction from a ventral side to a dorsal side of the pet, the lateral direction being orthogonal to the longitudinal direction, and the pet diaper comprising:
   a main body including an absorbent core and a tail hole configured to pass feces of the pet;
   a first elastic string attached to the main body in a stretched state and extending at least from a ventral-side edge of the tail hole to a dorsal-side edge of the absorbent core in the longitudinal direction; and
   a leakproof gather disposed at a position outside the absorbent core in the lateral direction, the leakproof gather comprising:
      a second elastic string that extends in the longitudinal direction;
      a standing portion that stands upright by contraction of the second elastic string; and
      a vertical fixed portion that serves as a standing fulcrum of the standing portion in the longitudinal direction, wherein
   the vertical fixed portion is fixed to the main body at a position outside the absorbent core in the longitudinal direction,
   the first elastic string is disposed at a position outside the leakproof gather in the lateral direction,
   a stretch ratio of the first elastic string is higher than a stretch ratio of the second elastic string,
   the main body further includes a tongue piece including:
      a base end portion coupled to a dorsal-side edge of the tail hole, and
      a distal end portion opposite to the base end portion,
   the tongue piece uncovers the tail hole when folded back with the base end portion as a fold line, and
   the distal end portion of the tongue piece is directed to the ventral side or in the lateral direction when the tongue piece is not folded back.

2. The pet diaper according to claim 1, wherein an opening width of the tail hole in the lateral direction continuously narrows toward the ventral side.

3. The pet diaper according to claim 1, wherein the first elastic string extends beyond a central position of the tail hole in the longitudinal direction.

4. The pet diaper according to claim 1, wherein the first elastic string extends beyond the dorsal-side edge of the tail hole in the longitudinal direction.

5. The pet diaper according to claim 1, wherein the first elastic string extends beyond a ventral-side edge of a virtual tail hole, wherein the virtual tail hole is set at a position line-symmetrical to the tail hole with respect to a center line of the main body in the longitudinal direction.

6. The pet diaper according to claim 1, further comprising:
   a pair of fastening tabs that are disposed closer to the ventral side than is the tail hole, and that extend outside lateral-side edges of the main body; and
   a target portion that is disposed closer to the dorsal side than is the tail hole to be engaged with the pair of fastening tabs, wherein
   the first elastic string extends beyond dorsal-side edges of the pair of fastening tabs in the longitudinal direction.

7. The pet diaper according to claim 6, wherein the first elastic string extends beyond a ventral-side edge of the target portion in the longitudinal direction.

8. The pet diaper according to claim 6, further comprising:
   a waist gather that is disposed closer to the ventral side than are the dorsal-side edges of the pair of fastening tabs, and that is stretchable in the lateral direction, wherein
   the first elastic string extends beyond a dorsal-side edge of the waist gather.

9. The pet diaper according to claim 1, wherein
   an effective length of the first elastic string is longer than an effective length of the second elastic string, and
   a largest opening width of the tail hole in the lateral direction is smaller than a distance between a center line of the main body in the lateral direction and an inner edge of the leakproof gather in the lateral direction.

10. The pet diaper according to claim 1, wherein
   a distance between the dorsal-side edge of the tail hole and the dorsal-side edge of the absorbent core in the longitudinal direction is longer than a distance between a lateral-side edge of the tail hole and the first elastic string in the lateral direction.

11. The pet diaper according to claim 1, wherein the tongue piece is entirely offset from the absorbent core.

12. The pet diaper according to claim 1, further comprising:
   a waist gather that is stretchable in the lateral direction, and is spaced away from the first elastic string in the lateral direction.

* * * * *